United States Patent [19]
Janjic et al.

[11] Patent Number: 5,849,479
[45] Date of Patent: *Dec. 15, 1998

[54] HIGH-AFFINITY OLIGONUCLEOTIDE LIGANDS TO VASCULAR ENDOTHELIAL GROWTH FACTOR (VEGF)

[75] Inventors: Nebojsa Janjic; Larry Gold, both of Boulder, Colo.

[73] Assignee: NeXstar Pharmaceuticals, Inc., Boulder, Colo.

[ * ] Notice: The term of this patent shall not extend beyond the expiration date of Pat. No. 5,459,015.

[21] Appl. No.: 233,012

[22] Filed: Apr. 25, 1994

Related U.S. Application Data

[63] Continuation-in-part of Ser. No. 714,131, Jun. 10, 1991, Pat. No. 5,475,096, which is a continuation-in-part of Ser. No. 536,428, Jun. 11, 1990, abandoned, and a continuation-in-part of Ser. No. 964,624, Oct. 21, 1992, Pat. No. 5,496,938.

[51] Int. Cl.$^6$ .............................. C12Q 1/68; C12P 19/34; C07H 21/02; C07H 21/04
[52] U.S. Cl. ................................ 435/6; 435/9.2; 53/25.4; 935/77; 935/78
[58] Field of Search ........................ 435/6, 91.2; 935/77, 935/78; 536/254

[56] References Cited

U.S. PATENT DOCUMENTS

| | | | |
|---|---|---|---|
| 5,270,163 | 12/1993 | Gold et al. ................................... | 435/6 |
| 5,459,015 | 10/1995 | Janjic et al. ................................ | 435/6 |
| 5,476,766 | 12/1995 | Gold et al. ................................... | 435/6 |

OTHER PUBLICATIONS

Breier et al. (1992) Development 114:521.
De Vries et al. (1992) Science 255:989.
Dvorak (1991) J. Exp. Med. 174:1275.
Ferrara et al. (1991) J. Cell. Biochem. 47:211.
Ferrara et al. (1992) Endocrine Rev. 13:18.
Folkman and Klagsbrun (1987) Science 235:442.
Galland et al. (1993) Oncogene 8:1233.
Gill and von Hippel (1989) Anal. Biochem. 182:319.
Gitay–Goren (1992) J. Biol. Chem. 267:6093.
Gutell et al. (1992) Nucl. Acids Res. 20:5785.
Jakeman et al. (1992) J. Clin. Invest. 89:244.
James et al. (1988) Meth. Enzymol. 180:227.
Kim et al. (1993) Nature 362:841.
Lowary et al. (1987) Nucleic Acids Res. 15:10483.
Milligan et al. (1987) Nucleic Acids Res. 15:8783.
Myoken et al. (1991) Proc. Natl. Acad. Sci. USA 88:5819.
Pepper et al. (1992) Biochem. Biophys. Res. Commun. 189:824.
Peretz et al. (19920 Biochem. Biophys. Res. Commun. 182:1340.
Plate et al. (1992) Nature 359:845.
Schneider et al. (1992) J. Mol. Biol. 228:862.
Senger et al. (1983) Science 219:983.
Shweiki et al. (1992) Nature 359:843.
Tuerk et al. (1990) J. Mol. Biol. 213:749.
Tuerk and Gold (1990) Science 249:505.
Unemori et al. (1993) J. Cell. Physiology 153:557.
Vaisman et al. (1990) J. Biol. Chem. 265:19461.
Yarus and Berg (1970) Anal. Biochem. 35:450.
Yeo et al. (1991) Biochem. Biophys. Res. Commun. 179:1568.

*Primary Examiner*—Stephanie W. Zoomer
*Attorney, Agent, or Firm*—Swanson & Bratschun LLC

[57] ABSTRACT

Methods are described for the identification and preparation of nucleic acid ligand ligands to vascular endothelial growth factor (VEGF). Included in the invention are specific RNA ligands to VEGF identified by the SELEX method.

6 Claims, 21 Drawing Sheets

Starting RNA:
5'-GGGAGCUCAGAAUAAACGCUCAA[-30N-]UUCGACAUGAGGCCCGGAUCCGGC-3'
(SEQ ID NO: 1)

PCR Primer 1:
        Hind III
        ------
5'-CCGAAGCTTAATACGACTCACTATAGGGAGCTCAGAATAAACGCTCAA-3'
                T7 Promoter
(SEQ ID NO: 2)

PCR Primer 2:
    Bam H1
    ------
5'-GCCGGATCCGGGCCTCATGTCGAA-3'
(SEQ ID NO: 3)

FIGURE 1

FAMILY 1

| | | | SEQ ID NO: |
|---|---|---|---|
| 1 | ucaaGAGUGAUGCU-CAUCCGCACUUGGUGACGUU | | 4 |
| 3 | (9) caaUACCGGCAUGUC-CAUGCUAGCGGGUAuucg | | 5 |
| 5 | aaUGCGUGUGUGACGCA-CAUCCGCACGCGCAuu | | 6 |
| 7 | (4) ucaaGGAGUGAUGCCCUAUCCGCACCUUGGCCCA | | 7 |
| 9 | ucaaGCUUGACNGCCCAUCCGAGCUUGAUCACGC | | 8 |
| 46 | aaacgcucaaUCCUUGAUGCG-GAUCCGAGGAUGGACGUUu | | 9 |
| 50 | ACACCGUCGACCUAUGAUGCG-CAUCCGCACUucgac | | 10 |
| 100 | aaCCGGUAGUCGCAUGGCCCAUCCGCGCCGGuucgac | | 11 |
| 107 | acgcucaaGUCAGCAUGGCCAUCCGCACCUUGACGUCUG | | 12 |
| 112 | CACGGUUCGAUCUGACGUU-CAUCCGCACUucga | | 13 |
| 119 | aacgcucaaGGAGCAGUGACGCA-CAUCCACACUCCAGCGuu | | 14 |

FAMILY 2

| | | SEQ ID NO: |
|---|---|---|
| 24 (3) | UUCGAAUGCCGAGGCUC--GUGCCUUGACGGGuuc | 15 |
| 34 | UCGCGAAUGCCGACCACU---CAGGUUGAUGGGuucg | 16 |
| 102 | ucaaUGCCGGCUGA---UCGGCUGAUGGGUUGACCG | 17 |
| 128 | GAAUGCCGAGCCCUAAGAGGCUUGAUGUGGuu | 18 |
| 27 | 5'-aaCCUUNAUGUGGCNCGAAC<br>UGCGUGCCGAGGuu-3' | 19 |
| 44 | 5'-aaGCUUGAUGGGUGACACAC<br>GUCAUGCCGAGCuu-3' | 20 |
| 55 | 5'-GUCGUCCUGCAUGGGCCGUAU<br>CGGUGCGCG-3' | 21 |

FAMILY 3

|  |  | SEQ ID NO: |
|---|---|---|
| 12 (7) | GCAGACGAAGGG-AACCUGCGUCUCGGCACCuucg | 22 |
| 28 | AAGGAGG-ANCCUGCGUCUCGGCACUCCGCA | 23 |
| 75 (1) | ucaaGGG-AACCUGCGUUUCGGCACCUUGUUCCGU | 24 |
| 137 | aaAUGUGGGUUACCUGCGUUUCGGCACCACGUuu | 25 |

FAMILY 4

|  |  | SEQ ID NO: |
|---|---|---|
| 6 | CGACGGUAGAGUCUGUCCGUCAUCCCCCA | 26 |
| 35 | AAAGACCCUGGUUGAGUCUGUCUGUCCCAGCCCGuu | 27 |
| 40 | GACCCAUCGUCAACGGUUGAGUCUGUCCGUucgacaugagg | 28 |
| 56 | gcucaaGGUUGAGUCUGUCCCUUCGAGUAUCUGAUC | 29 |
| 90 | UCGGACAGUUGGUUGAGUCUGUCCAACUUuu | 30 |
| 106 | GACCAUGUGACUGGUUGAGCCUGUCCAGuu | 31 |
| 138 | AACGGUUGAGUCUGUCCGUAAGAGAGCGC | 32 |

FAMILY 5

| | | SEQ ID NO: |
|---|---|---|
| 15 | UCGGAAUGUAGUUGACGUAUCCUUGU--CCGAuucgacau | 33 |
| 20 | aGGGUGUAGUUGGGACCUA--GUCCGCCGUACCuu | 34 |
| 21 | GGCAUAGUUGGGACCUC--GUCCGCCGUGCCC | 35 |
| 84 | gcucaaUAGUUGGAGGCCUGCCUGCCGUAGAGCG | 36 |

FAMILY 6

| | | SEQ ID NO: |
|---|---|---|
| 25 | aGGGGUUCUA-GUGGAGACUCUGCCCGGGCCCuu | 37 |
| 126 (2) | aACGGUUCUGUGGACUA-GCCGCCGGGCCGuu | 38 |

Family 3 (SEQ ID NO: 44)

Family 2 (SEQ ID NO: 43)

Family 1 (SEQ ID NO: 42)

Family 6
(SEQ ID NO: 47)

Family 5
(SEQ ID NO: 46)

Family 4
(SEQ ID NO: 45)

SELEX Experiment A

Starting RNA:
5'-GGGAGACAAGAAUAACGCUCAA[-30N-]UUCGACAGGAGGC
UCACAACAGGC-3'                                    (SEQ ID NO: 57)

PCR Primer 1:

5'-<u>TAATACGACTCACTATA</u>GGGAGACAAGAAUAACGCUCAA-3'
     T7 Promoter                                  (SEQ ID NO: 58)

PCR Primer 2:

5'-GCCTGTTGTGAGCCTCCTGTCGAA-3'      (SEQ ID NO: 59)

SELEX Experiment B:

Starting RNA:
5'-GGGAGGACGAUGCGG[-50N-]CAGACGACTCGCCCGA-3'
                                                  (SEQ ID NO: 60)

PCR Primer 1:

5'-<u>TAATACGACTCACTATA</u>GGGAGGACGAUGCGG-3'
     T7 Promoter                                  (SEQ ID NO: 61)

PCR Primer 2:

5'-TCGGGCGAGTCGTCTG-3'                (SEQ ID NO: 62)

FIGURE 8

```
FAMILY 1                                                                              SEQ ID NO:

14B               UGGCUGUGAUCAAUGCGGGGAGGUGAGGAAGGCCUUACAAAUCCUUCGG                    63
16B               UGUGAUCAAUGCGGUGCGGGGUAUGGAAUGGGGAGUCUGGAAUGCUGGCU                   64
17B               CGCUGUGUUCAAUGCGGGGAUCGGGCCCGAGGAUGAACAAAUGGCGGGU                    65
25B          UGUUGAGCAAGCACUCAUGUGGUCAAUGUGGGAGUGGGGAGCUGGUUGGGU                      66
28B          CAAGGGAGCGUUAGAGCCAUGUGGUCAAUGUGGGAUCGGGGAUUGGGGGU                       67
30B               CAUGGUUGUGAAACUGUGAAUCAAUGCGGGAGGGUAAAUGGUGGGU                      68
33B               AUGAGUGACACAUGUGAAUGCCUCAAUGUGGGGUAGGGGUAGCACGG                     69
34B               UGUGGUCAAUGUGGCUAAUGUGGGCUGGAGGCAUCCGUACUGGUGUGGU                   70
47B               CCGAGUUGUGUCAAUGUGGGCUCGGGUACGACGGGAACAGAGAUCUGG                    71
46B               GUGCUCAGCAUUGUGUGUCAAUGCGGGGAGUUUGGGUUGGCGACGG                      72

CONSENSUS:        UGUGNUCAAUGNGGGG                                                   73

FIGURE 9A

FAMILY 2

23B               CAUAGGCUUACAACAGAGCGGGGUUCUGAUGGUAGACGCCGGACGCCC                    74
51B               CGUCACAGAUCGUG                UAUGAUGGUAGACGCCGCCGUACCGCAUCCAGGCCAAGU

14A                             GCAACAGAGGCUGAUGGUAGACGCCGGCC-A                      75
17A                             AGAGUCGCUGAUGGUAGACGCCGGCG-GAUC                      76
23A                             GAGGCUGAUGGCAGACGC-GGCC-GAAGACA                      77
24A                             CCCUGAUGGUAGACGCCGGGGUGCCGGAA                        78

CONSENSUS:                      CUGAUGGUAGACGCCGG                                    80

FIGURE 9B
```

```
FAMILY 3                                                                                           SEQ ID NO:
7B  CAGUGCUGAACUAAUCGAACGGGUCAAGGAGGGUCGAACGAGAUCUGCCG                                                 81
26B           CACCUUCGUGGGGUCAAGGAGGAGGGUCGAGGCCCAGGAUCAACCGUGUG                                        82
54B                     GGUCAAGUUGGGUCGAGGAAGCGCUCCGAGUAUCGUAGUGUGCGACUGC                              83
8A             GAACUUGAUCGGGUCAAGGCGGGACGAA                                                            84
15A                UGGCGGGACCAAGGAGGGACGUGUAGGAAA                                                      85
16A           AAAAUGCACAAAAUCGGGUCAAGGAGGACGA                                                          86
45B   AUGGGUUCGUGUGUGAAUGGAGGAGGGUGGCUCGCAUGCUACUGUG                                                   87

CONSENSUS:                GGUCAAGGNGGG                                                                 88

FIGURE 9C

FAMILY 4                                                                                           SEQ ID NO:
43B  UGCACUAAGUCCGGGUAGUGGGAGUGGGUUGGGCCUGGAGUGCGC                                                     89
2A             AUCAAAGGGUAGAGGGUGGCUGUGUGGCAAG                                                         90
9A             AAUCGAGGGUAGCGGGCGGCUUGGCCAA                                                            91
60A            GCCUCGGAUCGGGCAGCGGGCUGGGAUGGCAA                                                        92
41A            AACGGAGUGGCUAAGGCGUUGGGUGCCAGGAA                                                        93

CONSENSUS:                 GGUAGNGGGNG                                                                 94

FIGURE 9D

FAMILY 5                                                                                           SEQ ID NO:
44B  AAC---CG-AGUCGUGUGGGGUUGGGCUCCAGUACAUCCCCGGUCUGGGUGU                                              95
50B  UAACAUACGCAGUCGUGUGGGUAGGGAU-CACAAACUGCG----UAUCGUGU                                              96

CONSENSUS:   AGUCGUGGGU-GGGG-U--CA                                                                    97

FIGURE 9E
```

| OTHER SEQUENCES | | SEQ ID NO: |
|---|---|---|
| 12A | AGUGUAGGAUAGGGAUGGGAGGUCCGGGA | 98 |
| 20A | ACUGUGGGCUCUAGGGCAGUGGGAGUGGAG | 99 |
| 48A | AGUGGGACAGGGAUUGCGGAGGGUUGAAGG | 100 |
| 11A | GUCAGGAGGACUGGAAGGUUGGGACUGGUGA | 101 |
| 54A | GCAGGAGAGAGGGUGUUGGGUGCGGAUACA | 102 |
| 8B | AGGGUAGGAGGCUAAGCAUAGUUCAGAGGAGGUGGCCGCCGUGCCCCCGUG | 103 |
| 32B | CAACAUUGGCACCAAUGCUCUGUGUUAAUGUGGGGGUUGGGAACGGCGCCG | 104 |
| 22B | ACCAAUGCAAUUGAGGGCAGUGGGGAAUUGGGCUCGUGUGU | 105 |
| 12B | GCAGUGGGUGAGGUCCGGGCACGAGAUUUGAACGGUUCUGGCUUGGU | 106 |
| 53B | GUGGUAGGUGUAGAGGGAUGGCGGAGUCCUAGUAGUUCUGUGCCUGGU | 107 |
| 13B | CGCGGGAGAGGGUAGUGGGGUGUUGGGACUUGGACAAGCAGCG | 108 |
| 1B | ACCCGCAUACGGACCGCGGAGGGGAAAUCUAGCCUCAGGGGUGGCGGGC | 109 |
| 5B | UGAAGAAGCGGGGACUGCACUGCGACGGGAUGGAGGACACGACUGCGGGGU | 110 |

FIGURE 9F

NITROCELLULOSE FILTER BINDERS:

| | | SEQ ID NO: |
|---|---|---|
| 22A | ACACCAGGAGAGUGGUUCGGGUGAGGACG | 111 |
| 33A | GUGGCUGAUGGCAGACGCCGGCUGCUGACG | 112 |
| 34A | UCGUGCCAGGACAUGGUGGCUCAUGGGUAA | 113 |
| 30A | AGGUACGGGGAGGAAGGAUAUAACGCGA | 114 |
| 32A | UGGAAAGGUGUGAAGAGAGGCAUCGGGGG | 115 |
| 38A | UCAAUGGCAGGAAGAGGAAGGAUGUGA | 116 |
| 45A | CAUGGGUAAGGGAGUGGGAGUGGUGAAUAG | 117 |
| 46A | GGAACGAGUAAGGCAGUGGGUGGUGAUGGC | 118 |
| 49A | UAGGGCAGAGGGAGUGGGUUAAGGCUGUGAU | 119 |
| 55A | GGGUAGUGGGAAGGGUAAGGCCGAGGUGG | 120 |
| 19A | AAUACACACCGCGGAAGGGAGGGUUGAAAA | 121 |
| 59A | AGACUACAGCGCGGGUUAGGGUUGAGGGAA | 122 |
| 61A | UACGAGCAAGCGGGCAGGAGGUUGAGGGAA | 123 |
| 40A | CAAGGUGUGGAGGAGAUACGAUCUGCAG | 124 |
| 18A | GGAGGGAAGGAGGGCAGGAUGGUCAG | 125 |
| 42A | UGAUGGCGGUAGUGGAGGUAAUGAGCGUGA | 126 |
| 1A | GCAACUGGGGCGGGGUGUAAGGA | 127 |
| 4A | GGAGGGGCCUAUAGGGGUGUAGGGUGUACGA | 128 |
| 36A | UAUAGGGUAGUGGGCUGUUAGGGCUAGGCACA | 129 |
| 21A | GAGGGUUGGAGGCAUGGGCAGGAACCGG | 130 |
| 44A | CGUAGAACUGGCGGGCCAGUGGGGGAUGC | 131 |
| 13A | UGAGGGGACGAGGGAUGUGGGGAGCGGGAC | 132 |
| 25A | CGAGGGAUGGGAGGCGUGUGAAGAGAUGCAA | 133 |
| 29A | GCAUCCGGGACAAGAUGGGUCGGUAAGGU | 134 |
| 47A | GUGUGCGGGGUCAAGACGGGUGGCGUGCG | 135 |
| 51A | UCAAACCAUGGCGGGGUUGGGUACGAGGAAC | 136 |
| 58A | CGAGUCCGAGGGAUGGGUGUGUGCGGCAA | 137 |
| 10A | CAGUGUCGAGAGAGAAGGGAGGAUGAAGAA | 138 |
| 2B | CACCACUACGCGGGAAGGGUAAGGGUGGAUUACAAGGUGAUUACAAGGUGACCGCUCCGU | 139 |
| 21B | UACGGUUAACGGGGUGGGUGUGGAGGACACAAAGCGCGUACCUGCCCC | 140 |
| 52B | AGGUCCUCGAGGGUCGCGGAGGUGUGUGGAGGUGGGCAUGGACCAAUAGAGCCGCGUG | 141 |
| 27B | AAACCAUCCUGCGGGAUGGAGGUGGAGGGGAAACACUAGAGCUUCGCCUG | 142 |
| 35B | AACUGGGUCACGCGGUUGAGGUGGAGGUGUAGAGGUGGGAUCAACGGUCGAGGG | 143 |
| 38B | CAUGAAAGUAGGGUUAUAGAAGGCCGUAGGAGGAGGUGGGUUGCGAGGGC | 144 |
| 10B | GUCUAUUGGGUAGGGUUUGCAAGAAUCCCACGAUAGGUAAAACAGUG | 145 |
| 19B | UGUAGGGAAGUACGAGAGUGGGGAGCGCCGUAUAGGUGGGGAGUGUGCU | 146 |

FIGURE 9G

SEQUENCE LISTING ( 1 ) GENERAL INFORMATION:

( i i i ) NUMBER OF SEQUENCES: 146

( 2 ) INFORMATION FOR SEQ ID NO:1:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGGAGCUCAG AAUAAACGCU CAANNNNNN NNNNNNNNN NNNNNNNNN           50

NNNUUCGACA UGAGGCCCGG AUCCGGC                                  77
```

( 2 ) INFORMATION FOR SEQ ID NO:2:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
CCGAAGCTTA ATACGACTCA CTATAGGGAG CTCAGAATAA ACGCTCAA          48
```

( 2 ) INFORMATION FOR SEQ ID NO:3:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

GCCGGATCCG GGCCTCATGT CGAA      24

( 2 ) INFORMATION FOR SEQ ID NO:4:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

GGGAGCUCAG AAUAAACGCU CAAGAGUGAU GCUCAUCCGC ACUUGGUGAC      50

GUUUUCGACA UGAGGCCCGG AUCCGGC      77

( 2 ) INFORMATION FOR SEQ ID NO:5:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

GGGAGCUCAG AAUAAACGCU CAAUACCGGC AUGCAUGUCC AUCGCUAGCG      50

GUAUUCGACA UGAGGCCCGG AUCCGGC      77

( 2 ) INFORMATION FOR SEQ ID NO:6:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

GGGAGCUCAG AAUAAACGCU CAAUGCGUGU UGUGACGCAC AUCCGCACGC      50

GCAUUCGACA UGAGGCCCGG AUCCGGC      77

( 2 ) INFORMATION FOR SEQ ID NO:7:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

GGGAGCUCAG AAUAAACGCU CAAGGAGUGA UGCCCUAUCC GCACCUUGGC      50

CCAUUCGACA UGAGGCCCGG AUCCGGC      77

( 2 ) INFORMATION FOR SEQ ID NO:8:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

GGGAGCUCAG AAUAAACGCU CAAGCUUGAC NGCCCAUCCG AGCUUGAUCA                     50

CGCUUCGACA UGAGGCCCGG AUCCGGC                                              77

( 2 ) INFORMATION FOR SEQ ID NO:9:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GGGAGCUCAG AAUAAACGCU CAAUCCUUGA UGCGGAUCCG AGGAUGGGAC                     50

GUUUUCGACA UGAGGCCCGG AUCCGGC                                              77

( 2 ) INFORMATION FOR SEQ ID NO:10:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GGGAGCUCAG AAUAAACGCU CAAACACCGU CGACCUAUGA UGCGCAUCCG                     50

CACUUCGACA UGAGGCCCGG AUCCGGC                                              77

( 2 ) INFORMATION FOR SEQ ID NO:11:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GGGAGCUCAG AAUAAACGCU CAACCGGUAG UCGCAUGGCC CAUCGCGCCC                     50

GGUUCGACAU GAGGCCCGGA UCCGGC                                               76

( 2 ) INFORMATION FOR SEQ ID NO:12:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GGGAGCUCAG AAUAAACGCU CAAGUCAGCA UGGCCCACCG CGCUUGACGU                     50

CUGUUCGACA UGAGGCCCGG AUCCGGC                                              77

( 2 ) INFORMATION FOR SEQ ID NO:13:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GGGAGCUCAG AAUAAACGCU CAACACGGUU CGAUCUGUGA CGUUCAUCCG                     50

CACUUCGACA UGAGGCCCGG AUCCGGC                                              77

( 2 ) INFORMATION FOR SEQ ID NO:14:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

```
GGGAGCUCAG  AAUAAACGCU  CAAGGAGCAG  UGACGCACAU  CCACACUCCA        50

GCGUUCGACA  UGAGGCCCGG  AUCCGGC                                   77
```

( 2 ) INFORMATION FOR SEQ ID NO:15:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

```
GGGAGCUCAG  AAUAAACGCU  CAAUUCGAAU  GCCGAGGCUC  GUGCCUUGAC        50

GGGUUCGACA  UGAGGCCCGG  AUCCGGC                                   77
```

( 2 ) INFORMATION FOR SEQ ID NO:16:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

```
GGGAGCUCAG  AAUAAACGCU  CAAUCGCGAA  UGCCGACCAC  UCAGGUUGAU        50

GGGUUCGACA  UGAGGCCCGG  AUCCGGC                                   77
```

( 2 ) INFORMATION FOR SEQ ID NO:17:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

```
GGGAGCUCAG  AAUAAACGCU  CAAUGCCGGC  CUGAUCGGCU  GAUGGGUUGA        50

CCGUUCGACA  UGAGGCCCGG  AUCCGGC                                   77
```

( 2 ) INFORMATION FOR SEQ ID NO:18:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:18:

```
GGGAGCUCAG  AAUAAACGCU  CAAGAAUGCC  GAGCCCUAAG  AGGCUUGAUG        50

UGGUUCGACA  UGAGGCCCGG  AUCCGGC                                   77
```

( 2 ) INFORMATION FOR SEQ ID NO:19:

( i ) SEQUENCE CHARACTERISTICS:

(A) LENGTH: 77 base pairs
(B) TYPE: nucleic acid
(C) STRANDEDNESS: single
(D) TOPOLOGY: linear (xi) SEQUENCE DESCRIPTION: SEQ ID NO:19:

| GGGAGCUCAG | AAUAAACGCU | CAACCUUNAU | GUGGCNCGAA | CUGCGUGCCG | 50 |
| AGGUUCGACA | UGAGGCCCGG | AUCCGGC | | | 77 |

(2) INFORMATION FOR SEQ ID NO:20:

(i) SEQUENCE CHARACTERISTICS:
      (A) LENGTH: 77 base pairs
      (B) TYPE: nucleic acid
      (C) STRANDEDNESS: single
      (D) TOPOLOGY: linear (xi) SEQUENCE DESCRIPTION: SEQ ID NO:20:

| GGGAGCUCAG | AAUAAACGCU | CAAGCUUGAU | GGGUGACACA | CGUCAUGCCG | 50 |
| AGCUUCGACA | UGAGGCCCGG | AUCCGGC | | | 77 |

(2) INFORMATION FOR SEQ ID NO:21:

(i) SEQUENCE CHARACTERISTICS:
      (A) LENGTH: 77 base pairs
      (B) TYPE: nucleic acid
      (C) STRANDEDNESS: single
      (D) TOPOLOGY: linear (xi) SEQUENCE DESCRIPTION: SEQ ID NO:21:

| GGGAGCUCAG | AAUAAACGCU | CAAGUCGUCC | UGCAUGGGCC | GUAUCGGUGC | 50 |
| GCGUUCGACA | UGAGGCCCGG | AUCCGGC | | | 77 |

(2) INFORMATION FOR SEQ ID NO:22:

(i) SEQUENCE CHARACTERISTICS:
      (A) LENGTH: 77 base pairs
      (B) TYPE: nucleic acid
      (C) STRANDEDNESS: single
      (D) TOPOLOGY: linear (xi) SEQUENCE DESCRIPTION: SEQ ID NO:22:

| GGGAGCUCAG | AAUAAACGCU | CAAGCAGACG | AAGGGAACCU | GCGUCUCGGC | 50 |
| ACCUUCGACA | UGAGGCCCGG | AUCCGGC | | | 77 |

(2) INFORMATION FOR SEQ ID NO:23:

(i) SEQUENCE CHARACTERISTICS:
      (A) LENGTH: 77 base pairs
      (B) TYPE: nucleic acid
      (C) STRANDEDNESS: single
      (D) TOPOLOGY: linear (xi) SEQUENCE DESCRIPTION: SEQ ID NO:23:

| GGGAGCUCAG | AAUAAACGCU | CAAAAGGAGG | ANCCUGCGUC | UCGGCACUCC | 50 |
| GCAUUCGACA | UGAGGCCCGG | AUCCGGC | | | 77 |

(2) INFORMATION FOR SEQ ID NO:24:

(i) SEQUENCE CHARACTERISTICS:
      (A) LENGTH: 77 base pairs
      (B) TYPE: nucleic acid
      (C) STRANDEDNESS: single
      (D) TOPOLOGY: linear ( x i ) SEQUENCE DESCRIPTION: SEQ ID NO:24:

GGGAGCUCAG AAUAAACGCU CAAGGGAACC UGCGUUUCGG CACCUUGUUC 50

CGUUUCGACA UGAGGCCCGG AUCCGGC 77

( 2 ) INFORMATION FOR SEQ ID NO:25:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

GGGAGCUCAG AAUAAACGCU CAAAAAUGUG GGUUACCUGC GUUUCGGCAC 50

CACGUUUCGA CAUGAGGCCC GGAUCCGGC 79

( 2 ) INFORMATION FOR SEQ ID NO:26:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

GGGAGCUCAG AAUAAACGCU CAACGACGGU AGAGUCUGUC CCGUCAUCCC 50

CCAUUCGACA UGAGGCCCGG AUCCGGC 77

( 2 ) INFORMATION FOR SEQ ID NO:27:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

GGGAGCUCAG AAUAAACGCU CAAAAAGACC CCUGGUUGAG UCUGUCCCAG 50

CCGUUCGACA UGAGGCCCGG AUCCGGC 77

( 2 ) INFORMATION FOR SEQ ID NO:28:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

GGGAGCUCAG AAUAAACGCU CAAGACCCAU CGUCAACGGU UGAGUCUGUC 50

CCGUUCGACA UGAGGCCCGG AUCCGGC 77

( 2 ) INFORMATION FOR SEQ ID NO:29:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

GGGAGCUCAG AAUAAACGCU CAAGGUUGAG UCUGUCCCUU CGAGUAUCUG 50

AUCUUCGACA UGAGGCCCGG AUCCGGC 77

( 2 ) INFORMATION FOR SEQ ID NO:30:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

```
GGGAGCUCAG  AAUAAACGCU  CAAUCGGACA  GUUGGUUGAG  UCUGUCCAA       50
CUUUUCGACA  UGAGGCCCGG  AUCCGGC                                 77
```

( 2 ) INFORMATION FOR SEQ ID NO:31:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

```
GGGAGCUCAG  AAUAAACGCU  CAAGACCAUG  UGACUGGUUG  AGCCUGUCCC      50
AGUUCGACAU  GAGGCCCGGA  UCCGGC                                  76
```

( 2 ) INFORMATION FOR SEQ ID NO:32:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

```
GGGAGCUCAG  AAUAAACGCU  CAAAACGGUU  GAGUCUGUCC  CGUAAGAGAG      50
CGCUUCGACA  UGAGGCCCGG  AUCCGGC                                 77
```

( 2 ) INFORMATION FOR SEQ ID NO:33:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

```
GGGAGCUCAG  AAUAAACGCU  CAAUCGGAAU  GUAGUUGACG  UAUCCUUGUC      50
CGAUUCGACA  UGAGGCCCGG  AUCCGGC                                 77
```

( 2 ) INFORMATION FOR SEQ ID NO:34:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

```
GGGAGCUCAG  AAUAAACGCU  CAAGGUGUA   GUUGGGACCU  AGUCCGCCGU      50
ACCUUCGACA  UGAGGCCCGG  AUCCGGC                                 77
```

( 2 ) INFORMATION FOR SEQ ID NO:35:

( i ) SEQUENCE CHARACTERISTICS:

(A) LENGTH: 77 base pairs
(B) TYPE: nucleic acid
(C) STRANDEDNESS: single
(D) TOPOLOGY: linear (xi) SEQUENCE DESCRIPTION: SEQ ID NO:35:

| GGGAGCUCAG | AAUAAACGCU | CAAGGCAUAG | UUGGGACCUC | GUCCGCCGUG | 50 |
| CCCUUCGACA | UGAGGCCCGG | AUCCGGC | | | 77 |

(2) INFORMATION FOR SEQ ID NO:36:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:36:

| GGGAGCUCAG | AAUAAACGCU | CAAUAGUUGG | AGGCCUGUCC | UCGCCGUAGA | 50 |
| GCGUUCGACA | UGAGGCCCGG | AUCCGGC | | | 77 |

(2) INFORMATION FOR SEQ ID NO:37:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:37:

| GGGAGCUCAG | AAUAAACGCU | CAAGGGGUUC | UAGUGGAGAC | UCUGCCGCGG | 50 |
| CCCUUCGACA | UGAGGCCCGG | AUCCGGC | | | 77 |

(2) INFORMATION FOR SEQ ID NO:38:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:38:

| GGGAGCUCAG | AAUAAACGCU | CAAACGGUUC | UGUGUGUGGA | CUAGCCGCGG | 50 |
| CCGUUCGACA | UGAGGCCCGG | AUCCGGC | | | 77 |

(2) INFORMATION FOR SEQ ID NO:39:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:39:

| GGGAGCUCAG | AAUAAACGCU | CAAGGAUGU | UUGGCUAUCU | CGGAUAGUGC | 50 |
| CCCUUCGACA | UGAGGCCCGG | AUCCGGC | | | 77 |

(2) INFORMATION FOR SEQ ID NO:40:

(i) SEQUENCE CHARACTERISTICS:
        (A) LENGTH: 77 base pairs
        (B) TYPE: nucleic acid
        (C) STRANDEDNESS: single
        (D) TOPOLOGY: linear ( x i ) SEQUENCE DESCRIPTION: SEQ ID NO:40:

GGGAGCUCAG AAUAAACGCU CAAGCUUAAU ACGACUCACU NUAGGGAGCU     50

CAGUUCGACA UGAGGCCCGG AUCCGGC     77

( 2 ) INFORMATION FOR SEQ ID NO:41:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

GGGAGCUCAG AAUAAACGCU CAAUUGAGUG AUGUGCUUGA CGUAUCGCUG     50

CACUUCGACA UGAGGCCCGG AUCCGGC     77

( 2 ) INFORMATION FOR SEQ ID NO:42:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( A ) NAME/KEY: N
        ( B ) LOCATION: 15
        ( C ) OTHER INFORMATION: This symbol stands
            for the complimentary base for the N
            located in position 1

( x i ) SEQUENCE DESCRIPTION: SEQ ID NO:42:

NUGAUGVNCA UCCGN     15

( 2 ) INFORMATION FOR SEQ ID NO:43:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( A ) NAME/KEY: S
        ( B ) LOCATION: 11 and 12
        ( C ) OTHER INFORMATION: This symbol stands
            for the complimentary base for the S
            located in positions 9 and 10

( x i ) SEQUENCE DESCRIPTION: SEQ ID NO:43:

AAUGCCGASS SSUUGAUGGG UU     22

( 2 ) INFORMATION FOR SEQ ID NO:44:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( A ) NAME/KEY: H
        ( B ) LOCATION: 24
        ( C ) OTHER INFORMATION: This symbol stands for the complimentary base for the D
located in position 2

( i x ) FEATURE:
      ( A ) NAME/KEY: Y
      ( B ) LOCATION: 25
      ( C ) OTHER INFORMATION: This symbol stands
for the complimentary base for the R
located in position 25

( i i ) MOLECULE TYPE: RNA ( x i ) SEQUENCE DESCRIPTION: SEQ ID NO:44:

R D G G G A A C C U   G C G U Y U C G G C   A C C H Y                                                   2 5

( 2 ) INFORMATION FOR SEQ ID NO:45:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( A ) NAME/KEY: D
        ( B ) LOCATION: 18 and 19
        ( C ) OTHER INFORMATION: This symbol stands
for the complimentary base for the H
located in positions 1 and 2

( x i ) SEQUENCE DESCRIPTION: SEQ ID NO:45:

H H G G U U G A G U   C U G U C C C D D                                                                 1 9

( 2 ) INFORMATION FOR SEQ ID NO:46:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( A ) NAME/KEY: N
        ( B ) LOCATION: 18-20 and 27
        ( C ) OTHER INFORMATION: This symbol stands
for the complimentary base for the N
located in positions 1 and 10-12

( x i ) SEQUENCE DESCRIPTION: SEQ ID NO:46:

N R U A G U U G G N   N N C U N S U N N N   C G C C G U N                                     2 7

( 2 ) INFORMATION FOR SEQ ID NO:47:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( A ) NAME/KEY: M
        ( B ) LOCATION: 20
        ( C ) OTHER INFORMATION: This symbol stands
for the complimentary base for the K
located in position 14

( i x ) FEATURE:
        ( A ) NAME/KEY: S (B) LOCATION: 31
(C) OTHER INFORMATION: This symbol stands
    for the complimentary base for the S
    located in position 2

(xi) SEQUENCE DESCRIPTION: SEQ ID NO:47:

RSGGUUUCRU GUGKRGACUM UGCCGCGGCC SU                32

(2) INFORMATION FOR SEQ ID NO:48:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (xi) SEQUENCE DESCRIPTION: SEQ ID NO:48:

GGGAACCUGC GUYUCGGCAC C                            21

(2) INFORMATION FOR SEQ ID NO:49:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:49:

GGUUGAGUCU GUCCC                                   15

(2) INFORMATION FOR SEQ ID NO:50:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (xi) SEQUENCE DESCRIPTION: SEQ ID NO:50:

AAGCAGACGA AGGGAACCUG CGUCUCGGCA CCUUCGACAU         40

(2) INFORMATION FOR SEQ ID NO:51:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (xi) SEQUENCE DESCRIPTION: SEQ ID NO:51:

GGCCGGUAGU CGCAUGGCCC AUCGCGCCCG G                 31

(2) INFORMATION FOR SEQ ID NO:52:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (xi) SEQUENCE DESCRIPTION: SEQ ID NO:52:

GGAAGCUUGA UGGGUGACAC ACGUCAUGCC GAGCU             35

(2) INFORMATION FOR SEQ ID NO:53:

(i) SEQUENCE CHARACTERISTICS:
      (A) LENGTH: 29 base pairs
      (B) TYPE: nucleic acid ( C ) STRANDEDNESS: single
        ( D ) TOPOLOGY: linear ( x i ) SEQUENCE DESCRIPTION: SEQ ID NO:53:

GGAAGGGAAC CUGCGUCUCG GCACCUUCG                                         29

( 2 ) INFORMATION FOR SEQ ID NO:54:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

GGUCAACGGU UGAGUCUGUC CCGUUCGAC                                         29

( 2 ) INFORMATION FOR SEQ ID NO:55:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

GGCUCAAUAG UUGGAGGCCU GUCCUCGCCG UAGAGC                                 36

( 2 ) INFORMATION FOR SEQ ID NO:56:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

GGAACGGUUC UGUGUGUGGA CUAGCCGCGG CCGUU                                  35

( 2 ) INFORMATION FOR SEQ ID NO:57:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:57:

GGGAGACAAG AAUAACGCUC AANNNNNNNN NNNNNNNNN NNNNNNNNN                    50

NNUUCGACAG GAGGCUCACA ACAGGC                                            76

( 2 ) INFORMATION FOR SEQ ID NO:58:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:

( D ) OTHER INFORMATION: All U'S are 2'-NH2 uracil ( x i ) SEQUENCE DESCRIPTION: SEQ ID NO:58:

TAATACGACT CACTATAGGG AGACAAGAAU AACGCUCAA 39

( 2 ) INFORMATION FOR SEQ ID NO:59:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:59:

GCCTGTTGTG AGCCTCCTGT CGAA 24

( 2 ) INFORMATION FOR SEQ ID NO:60:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:60:

GGGAGGACGA UGCGGNNNNN NNNNNNNNNN NNNNNNNNNN NNNNNNNNNN 50

NNNNNNNNNN NNNNNCAGAC GACTCGCCCG A 81

( 2 ) INFORMATION FOR SEQ ID NO:61:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:61:

TAATACGACT CACTATAGGG AGGACGAUGC GG 32

( 2 ) INFORMATION FOR SEQ ID NO:62:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:62:

TCGGGCGAGT CGTCTG                                                                                    16

( 2 ) INFORMATION FOR SEQ ID NO:63:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:63:

GGGAGGACGA UGCGGUGGCU GUGAUCAAUG CGGGGAGGUG AGGAAGGGCC                                                50

UUACAAAUCC UUCGGCAGAC GACTCGCCCG A                                                                    81

( 2 ) INFORMATION FOR SEQ ID NO:64:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:64:

GGGAGGACGA UGCGGUGUGA UCAAUGCGGU GGCGGGGUAU GGAUGGGAGU                                                50

CUGGAAUGCU GCGCUCAGAC GACTCGCCCG A                                                                    81

( 2 ) INFORMATION FOR SEQ ID NO:65:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:65:

GGGAGGACGA UGCGGCGCUG UGUUCAAUGC GGGGAUCGGG CCGGAGGAUG                                                50

AACAAAUGGC GGGUCAGACG ACTCGCCCGA                                                                      80

( 2 ) INFORMATION FOR SEQ ID NO:66:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:

(D) OTHER INFORMATION: All U'S are 2'-NH2 uracil (x i) SEQUENCE DESCRIPTION: SEQ ID NO:66:

GGGAGGACGA UGCGGUGUUG AGCAAGCACU CAUGUGGUCA AUGUGGGAGU      50
GGGAGCUGGU GGGGUCAGAC GACTCGCCCG A                          81

(2) INFORMATION FOR SEQ ID NO:67:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (x i) SEQUENCE DESCRIPTION: SEQ ID NO:67:

GGGAGGACGA UGCGGCAAGG GAGCGUUAGA GCCAUGUGGU CAAUGAGGGG      50
UGGGAUUGGU UGGGUCAGAC GACTCGCCCG A                          81

(2) INFORMATION FOR SEQ ID NO:68:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (x i) SEQUENCE DESCRIPTION: SEQ ID NO:68:

GGGAGGACGA UGCGGCAUGG UUGUGAACUG UUGUGAUCAA UGCGGGGAGG      50
GUAAUGGUGG GUGGUCAGAC GACTCGCCCG A                          81

(2) INFORMATION FOR SEQ ID NO:69:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (x i) SEQUENCE DESCRIPTION: SEQ ID NO:69:

GGGAGGACGA UGCGGAUGAG UGACACAUGU GCUCAAUGCG GGGUGGGUUG      50
GUAGGGGUAG CACGGCAGAC GACTCGCCCG A                          81

(2) INFORMATION FOR SEQ ID NO:70:

(i) SEQUENCE CHARACTERISTICS:
        (A) LENGTH: 80 base pairs
        (B) TYPE: nucleic acid
        (C) STRANDEDNESS: single
        (D) TOPOLOGY: linear 5,849,479

-continued ( i x ) FEATURE:
  ( D ) OTHER INFORMATION: All C'S are 2'-NH2 cytosine ( i x ) FEATURE:
  ( D ) OTHER INFORMATION: All U'S are 2'-NH2 uracil ( x i ) SEQUENCE DESCRIPTION: SEQ ID NO:70:

GGGAGGACGA UGCGGUGUGG UCAAUGUGGG GUAGGGCUGG UAGGGCAUUC        50

CGUACUGGUG UGGUCAGACG ACTCGCCCGA        80

( 2 ) INFORMATION FOR SEQ ID NO:71:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH2 cytosine ( i x ) FEATURE:
    ( D ) OTHER INFORMATION: All U'S are 2'-NH2 uracil ( x i ) SEQUENCE DESCRIPTION: SEQ ID NO:71:

GGGAGGACGA UGCGGCCGAG UUGUGCUCAA UGUGGGGUCU GGGUACGGAC        50

GGGAACAGAU CUGGCAGACG ACTCGCCCGA        80

( 2 ) INFORMATION FOR SEQ ID NO:72:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH2 cytosine ( i x ) FEATURE:
    ( D ) OTHER INFORMATION: All U'S are 2'-NH2 uracil ( x i ) SEQUENCE DESCRIPTION: SEQ ID NO:72:

GGGAGGACGA UGCGGGUGCU CAGCAUUGUG UGCUCAAUGC GGGGGAGUUU        50

GGGUUGGCGA CGGCAGACGA CTCGCCCGA        79

( 2 ) INFORMATION FOR SEQ ID NO:73:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH2 cytosine ( i x ) FEATURE:
    ( D ) OTHER INFORMATION: All U'S are 2'-NH2 uracil ( x i ) SEQUENCE DESCRIPTION: SEQ ID NO:73:

UGUGNUCAAU GNGGGG        16

( 2 ) INFORMATION FOR SEQ ID NO:74:

( i ) SEQUENCE CHARACTERISTICS:
    ( A ) LENGTH: 81 base pairs
    ( B ) TYPE: nucleic acid
    ( C ) STRANDEDNESS: single (D) TOPOLOGY: linear (ix) FEATURE:
(D) OTHER INFORMATION: All C'S are 2'-NH2 cytosine (ix) FEATURE:
(D) OTHER INFORMATION: All U'S are 2'-NH2 uracil (xi) SEQUENCE DESCRIPTION: SEQ ID NO:74:

GGGAGGACGA UGCGGCAUAG GCUUACAACA GAGCGGGGGU UCUGAUGGUA         50

GACGCCGGGA CGCCCCAGAC GACTCGCCCG A                              81

(2) INFORMATION FOR SEQ ID NO:75:

(i) SEQUENCE CHARACTERISTICS:
(A) LENGTH: 80 base pairs
(B) TYPE: nucleic acid
(C) STRANDEDNESS: single
(D) TOPOLOGY: linear (ix) FEATURE:
(D) OTHER INFORMATION: All C'S are 2'-NH2 cytosine (ix) FEATURE:
(D) OTHER INFORMATION: All U'S are 2'-NH2 uracil (xi) SEQUENCE DESCRIPTION: SEQ ID NO:75:

GGGAGGACGA UGCGGUAUGA UGGUAGACGC CGUACCGCAU CAGGCCAAGU         50

CGUCACAGAU CGUGCAGACG ACTCGCCCGA                                80

(2) INFORMATION FOR SEQ ID NO:76:

(i) SEQUENCE CHARACTERISTICS:
(A) LENGTH: 76 base pairs
(B) TYPE: nucleic acid
(C) STRANDEDNESS: single
(D) TOPOLOGY: linear (ix) FEATURE:
(D) OTHER INFORMATION: All C'S are 2'-NH2 cytosine (ix) FEATURE:
(D) OTHER INFORMATION: All U'S are 2'-NH2 uracil (xi) SEQUENCE DESCRIPTION: SEQ ID NO:76:

GGGAGACAAG AAUAACGCUC AAGCAACAGA GGCUGAUGGU AGACGCCGGC         50

CAUUCGACAG GAGGCUCACA ACAGGC                                    76

(2) INFORMATION FOR SEQ ID NO:77:

(i) SEQUENCE CHARACTERISTICS:
(A) LENGTH: 76 base pairs
(B) TYPE: nucleic acid
(C) STRANDEDNESS: single
(D) TOPOLOGY: linear (ix) FEATURE:
(D) OTHER INFORMATION: All C'S are 2'-NH2 cytosine (ix) FEATURE:
(D) OTHER INFORMATION: All U'S are 2'-NH2 uracil (xi) SEQUENCE DESCRIPTION: SEQ ID NO:77:

GGGAGACAAG AAUAACGCUC AAAGAGUCGC UGAUGGUAGA CGCCGGCGGA         50

UCUUCGACAG GAGGCUCACA ACAGGC                                    76

(2) INFORMATION FOR SEQ ID NO:78:

( i ) SEQUENCE CHARACTERISTICS:
    ( A ) LENGTH: 75 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH2 cytosine ( i x ) FEATURE:
    ( D ) OTHER INFORMATION: All U'S are 2'-NH2 uracil ( x i ) SEQUENCE DESCRIPTION: SEQ ID NO:78:

GGGAGACAAG AAUAACGCUC AAGAGGCUGA UGGCAGACGC GGCCGAAGAC         50

AUUCGACAGG AGGCUCACAA CAGGC                                   75

( 2 ) INFORMATION FOR SEQ ID NO:79:

( i ) SEQUENCE CHARACTERISTICS:
    ( A ) LENGTH: 75 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH2 cytosine ( i x ) FEATURE:
    ( D ) OTHER INFORMATION: All U'S are 2'-NH2 uracil ( x i ) SEQUENCE DESCRIPTION: SEQ ID NO:79:

GGGAGACAAG AAUAACGCUC AACCCUGAUG GUAGACGCCG GGGUGCCGGA         50

AUUCGACAGG AGGCUCACAA CAGGC                                   75

( 2 ) INFORMATION FOR SEQ ID NO:80:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH2 cytosine ( i x ) FEATURE:
    ( D ) OTHER INFORMATION: All U'S are 2'-NH2 uracil ( x i ) SEQUENCE DESCRIPTION: SEQ ID NO:80:

CUGAUGGUAG ACGCCGG                                            17

( 2 ) INFORMATION FOR SEQ ID NO:81:

( i ) SEQUENCE CHARACTERISTICS:
    ( A ) LENGTH: 82 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH2 cytosine ( i x ) FEATURE:
    ( D ) OTHER INFORMATION: All U'S are 2'-NH2 uracil ( x i ) SEQUENCE DESCRIPTION: SEQ ID NO:81:

GGGAGGACGA UGCGGCAGUG CUGAACUAAU CGAACGGGGU CAAGGAGGGU         50

CGAACGAGAU CUGCCGCAGA CGACTCGCCC GA                           82

( 2 ) INFORMATION FOR SEQ ID NO:82:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:82:

```
GGGAGGACGA UGCGGCACCU UCGUGGGUC  AAGGAGGGUC GCGAGGCCGC          50
AGGAUCAACC GUGUGCAGAC GACTCGCCCG A                              81
```

( 2 ) INFORMATION FOR SEQ ID NO:83:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:83:

```
GGGAGGACGA UGCGGGGUCA AGUUGGGUCG AGGAAGCGCU CCCGAGUAUC          50
GUAGUGUGCG ACUGCCAGAC GACTCGCCCG A                              81
```

( 2 ) INFORMATION FOR SEQ ID NO:84:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:84:

```
GGGAGACAAG AAUAACGCUC AAGAACUUGA UCGGGGUCAA GGCGGGACGA          50
AUUCGACAGG AGGCUCACAA CAGGC                                     75
```

( 2 ) INFORMATION FOR SEQ ID NO:85:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:85:

```
GGGAGACAAG AAUAACGCUC AAUGGCGGGA CCAAGGAGGG ACGUGUAGGA          50
```

```
AAUUCGACAG  GAGGCUCACA  ACAGGC                                                    76
```

( 2 ) INFORMATION FOR SEQ ID NO:86:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:86:

```
GGGAGACAAG  AAUAACGCUC  AAAAAAUGCA  CAAAUCGGGG  UCAAGGAGGG                        50

ACGAUUCGAC  AGGAGGCUCA  CAACAGGC                                                  78
```

( 2 ) INFORMATION FOR SEQ ID NO:87:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:87:

```
GGGAGGACGA  UGCGGAUGGG  UUCGUGUGGU  GAAUGGAGGA  GGUGGGCUCG                        50

CAUGCUACUG  UGCAGACGAC  TCGCCCGA                                                  78
```

( 2 ) INFORMATION FOR SEQ ID NO:88:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:88:

```
GGUCAAGGNG  GG                                                                    12
```

( 2 ) INFORMATION FOR SEQ ID NO:89:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:89:

```
GGGAGGACGA UGCGGUGCAC UAAGUCCGGG UAGUGGGAGU GGUUGGGCCU           50

GGAGUGCGCC AGACGACTCG CCCGA                                     75
```

( 2 ) INFORMATION FOR SEQ ID NO:90:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:90:

```
GGGAGACAAG AAUAACGCUC AAAUCAAAGG GUAGAGGGUG GGCUGUGGCA           50

AGUUCGACAG GAGGCUCACA ACAGGC                                    76
```

( 2 ) INFORMATION FOR SEQ ID NO:91:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:91:

```
GGGAGACAAG AAUAACGCUC AAAAUCGAGG GUAGCGGGCG CGGCUUGGCC           50

AAUUCGACAG GAGGCUCACA ACAGGC                                    76
```

( 2 ) INFORMATION FOR SEQ ID NO:92:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:92:

```
GGGAGACAAG AAUAACGCUC AAGCCUCGGA UCGGGCAGCG GGUGGGAUGG           50

CAAUUCGACA GGAGGCUCAC AACAGGC                                   77
```

( 2 ) INFORMATION FOR SEQ ID NO:93:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
    ( D ) OTHER INFORMATION: All U'S are 2'-NH2 uracil ( x i ) SEQUENCE DESCRIPTION: SEQ ID NO:93:

GGGAGACAAG AAUAACGCUC AAAACGGAGU GGUAGGCGUU GGGUGCCAGG                50

AAUUCGACAG GAGGCUCACA ACAGGC                                         76

( 2 ) INFORMATION FOR SEQ ID NO:94:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:94:

GGUAGNGGGN G                                                         11

( 2 ) INFORMATION FOR SEQ ID NO:95:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:95:

GGGAGGACGA UGCGGAACCG AGUCGUGUGG GUUGGGGCUC CAGUACAUCC                50

CCGGUCUGGG UGUCAGACGA CTCGCCCGA                                      79

( 2 ) INFORMATION FOR SEQ ID NO:96:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:96:

GGGAGGACGA UGCGGUAACA UACGCAGUCG UGUGGUAGG GGAUCACAAA                 50

CUGCGUAUCG UGUCAGACGA CTCGCCCGA                                      79

( 2 ) INFORMATION FOR SEQ ID NO:97:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i x ) FEATURE:

( D ) OTHER INFORMATION: All C'S are 2'-NH2 cytosine ( i x ) FEATURE:
( D ) OTHER INFORMATION: All U'S are 2'-NH2 uracil ( x i ) SEQUENCE DESCRIPTION: SEQ ID NO:97:

GGGAGACAAG AAUAACGCUC AAAGUCGUGU GGGUGGGGUC AUUCGACAGG 50

AGGCUCACAA CAGGC 65

( 2 ) INFORMATION FOR SEQ ID NO:98:

( i ) SEQUENCE CHARACTERISTICS:
( A ) LENGTH: 76 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH2 cytosine ( i x ) FEATURE:
( D ) OTHER INFORMATION: All U'S are 2'-NH2 uracil ( x i ) SEQUENCE DESCRIPTION: SEQ ID NO:98:

GGGAGACAAG AAUAACGCUC AAAGUGUAGG AUAGGGGAUG GGAGGUCCGG 50

GAUUCGACAG GAGGCUCACA ACAGGC 76

( 2 ) INFORMATION FOR SEQ ID NO:99:

( i ) SEQUENCE CHARACTERISTICS:
( A ) LENGTH: 76 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH2 cytosine ( i x ) FEATURE:
( D ) OTHER INFORMATION: All U'S are 2'-NH2 uracil ( x i ) SEQUENCE DESCRIPTION: SEQ ID NO:99:

GGGAGACAAG AAUAACGCUC AAACUGUGGG CUCUAGGGCA GUGGGAGUGG 50

AGUUCGACAG GAGGCUCACA ACAGGC 76

( 2 ) INFORMATION FOR SEQ ID NO:100:

( i ) SEQUENCE CHARACTERISTICS:
( A ) LENGTH: 76 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH2 cytosine ( i x ) FEATURE:
( D ) OTHER INFORMATION: All U'S are 2'-NH2 uracil ( x i ) SEQUENCE DESCRIPTION: SEQ ID NO:100:

GGGAGACAAG AAUAACGCUC AAAGUGGGAC AGGGAUUGCG GAGGGUGGAA 50

GGUUCGACAG GAGGCUCACA ACAGGC 76

( 2 ) INFORMATION FOR SEQ ID NO:101:

( i ) SEQUENCE CHARACTERISTICS:
( A ) LENGTH: 76 base pairs
( B ) TYPE: nucleic acid ( C ) STRANDEDNESS: single
( D ) TOPOLOGY: linear ( i x ) FEATURE:
( D ) OTHER INFORMATION: All C'S are 2'-NH2 cytosine ( i x ) FEATURE:
( D ) OTHER INFORMATION: All U'S are 2'-NH2 uracil ( x i ) SEQUENCE DESCRIPTION: SEQ ID NO:101:

GGGAGACAAG AAUAACGCUC AAGUCAGGAG GACUGGAAGG UGGGACUGGU    50

GAUUCGACAG GAGGCUCACA ACAGGC    76

( 2 ) INFORMATION FOR SEQ ID NO:102:

( i ) SEQUENCE CHARACTERISTICS:
( A ) LENGTH: 76 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH2 cytosine ( i x ) FEATURE:
( D ) OTHER INFORMATION: All U'S are 2'-NH2 uracil ( x i ) SEQUENCE DESCRIPTION: SEQ ID NO:102:

GGGAGACAAG AAUAACGCUC AAGCAGGAGA GAGGGUGUUG GGUGCGGAUA    50

CAUUCGACAG GAGGCUCACA ACAGGC    76

( 2 ) INFORMATION FOR SEQ ID NO:103:

( i ) SEQUENCE CHARACTERISTICS:
( A ) LENGTH: 80 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH2 cytosine ( i x ) FEATURE:
( D ) OTHER INFORMATION: All U'S are 2'-NH2 uracil ( x i ) SEQUENCE DESCRIPTION: SEQ ID NO:103:

GGGAGGACGA UGCGGAGGGU AGGAGGCUAA GCAUAGUUCA GAGGAGGUGG    50

CGCGUGCCCC CGUGCAGACG ACTCGCCCGA    80

( 2 ) INFORMATION FOR SEQ ID NO:104:

( i ) SEQUENCE CHARACTERISTICS:
( A ) LENGTH: 80 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH2 cytosine ( i x ) FEATURE:
( D ) OTHER INFORMATION: All U'S are 2'-NH2 uracil ( x i ) SEQUENCE DESCRIPTION: SEQ ID NO:104:

GGGAGGACGA UGCGGCAACA UUGGCACCAA UGCUCUGUGU UAAUGUGGGG    50

UGGGAACGGC GCCGCAGACG ACTCGCCCGA    80

( 2 ) INFORMATION FOR SEQ ID NO:105:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH2 cytosine ( i x ) FEATURE:
    ( D ) OTHER INFORMATION: All U'S are 2'-NH2 uracil ( x i ) SEQUENCE DESCRIPTION: SEQ ID NO:105:

```
GGGAGGACGA  UGCGGACCAA  UGAUUGCAAU  GAGGGCAGUG  GGGGGGAAUU      50
GGGCUCGUGU  GGUCAGACGA  CTCGCCCGA                               79
```

( 2 ) INFORMATION FOR SEQ ID NO:106:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:106:

```
GGGAGGACGA  UGCGGGCAGU  GGGUGAGGUC  CGGGCACGAU  UGAGUUUGAA      50
CGGUUCUGGC  UUGGUCAGAC  GACTCGCCCG  A                           81
```

( 2 ) INFORMATION FOR SEQ ID NO:107:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:107:

```
GGGAGGACGA  UGCGGGUGGU  AGGUGUAGAG  UGGAUGGCGG  AGGUCCUAGU      50
AGUUCUGUGC  CUGGUCAGAC  GACTCGCCCG  A                           81
```

( 2 ) INFORMATION FOR SEQ ID NO:108:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:108:

```
GGGAGGACGA  UGCGGCGCGG  GAGAGGGUAG  UGGGUGUGGU  GCUUGGACAA      50
```

GCAGCGCAGA CGACTCGCCC GA 72

( 2 ) INFORMATION FOR SEQ ID NO:109:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:109:

GGGAGGACGA UGCGGACCCG CAUACGGACC GCGGAGGGGG AAAUCUAGCC 50

UCAGGGGUGG CGGGCCAGAC GACTCGCCCG A 81

( 2 ) INFORMATION FOR SEQ ID NO:110:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:110:

GGGAGGACGA UGCGGUGAAG AAGCGGGGAC UGCACGACGG GAUGGAGGGA 50

CACGACUGCG GGGUCAGACG ACTCGCCCGA 80

( 2 ) INFORMATION FOR SEQ ID NO:111:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:111:

GGGAGACAAG AAUAACGCUC AAACACCAGG AGAGUGGGUU CGGGUGAGGA 50

CGUUCGACAG GAGGCUCACA ACAGGC 76

( 2 ) INFORMATION FOR SEQ ID NO:112:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:112:

GGGAGACAAG AAUAACGCUC AAGUGGCUGA UGGCAGACGC CGGCUGCUGA 50

CGUUCGACAG GAGGCUCACA ACAGGC 76

( 2 ) INFORMATION FOR SEQ ID NO:113:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:113:

GGGAGACAAG AAUAACGCUC AAUCGUGCCA GGACAUGGUG GCUCAUGGGU 50

AAUUCGACAG GAGGCUCACA ACAGGC 76

( 2 ) INFORMATION FOR SEQ ID NO:114:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:114:

GGGAGACAAG AAUAACGCUC AAAGGUACGG GGGAGGGAAG GAUAUAACGC 50

GAUUCGACAG GAGGCUCACA ACAGGC 76

( 2 ) INFORMATION FOR SEQ ID NO:115:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:115:

GGGAGACAAG AAUAACGCUC AAUGGAAAGG UGUGGAAAGA GGCAUCGGGG 50

GGUUCGACAG GAGGCUCACA ACAGGC 76

( 2 ) INFORMATION FOR SEQ ID NO:116:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
　　　　( D ) OTHER INFORMATION: All U'S are 2'-NH2 uracil ( x i ) SEQUENCE DESCRIPTION: SEQ ID NO:116:

GGGAGACAAG AAUAACGCUC AAUCAAUGGG CAGGAAGAGG GAAGGGAUGU　　　　50

GAUUCGACAG GAGGCUCACA ACAGGC　　　　76

( 2 ) INFORMATION FOR SEQ ID NO:117:

( i ) SEQUENCE CHARACTERISTICS:
　　　　　　( A ) LENGTH: 76 base pairs
　　　　　　( B ) TYPE: nucleic acid
　　　　　　( C ) STRANDEDNESS: single
　　　　　　( D ) TOPOLOGY: linear ( i x ) FEATURE:
　　　　　　( D ) OTHER INFORMATION: All C'S are 2'-NH2 cytosine ( i x ) FEATURE:
　　　　　　( D ) OTHER INFORMATION: All U'S are 2'-NH2 uracil ( x i ) SEQUENCE DESCRIPTION: SEQ ID NO:117:

GGGAGACAAG AAUAACGCUC AACAUGGGUA AGGGAGUGGG AGUGGUGAAU　　　　50

AGUUCGACAG GAGGCUCACA ACAGGC　　　　76

( 2 ) INFORMATION FOR SEQ ID NO:118:

( i ) SEQUENCE CHARACTERISTICS:
　　　　　　( A ) LENGTH: 76 base pairs
　　　　　　( B ) TYPE: nucleic acid
　　　　　　( C ) STRANDEDNESS: single
　　　　　　( D ) TOPOLOGY: linear ( i x ) FEATURE:
　　　　　　( D ) OTHER INFORMATION: All C'S are 2'-NH2 cytosine ( i x ) FEATURE:
　　　　　　( D ) OTHER INFORMATION: All U'S are 2'-NH2 uracil ( x i ) SEQUENCE DESCRIPTION: SEQ ID NO:118:

GGGAGACAAG AAUAACGCUC AAGGAACGAG UAGGGCAGUG GGUGGUGAUG　　　　50

GCUUCGACAG GAGGCUCACA ACAGGC　　　　76

( 2 ) INFORMATION FOR SEQ ID NO:119:

( i ) SEQUENCE CHARACTERISTICS:
　　　　　　( A ) LENGTH: 76 base pairs
　　　　　　( B ) TYPE: nucleic acid
　　　　　　( C ) STRANDEDNESS: single
　　　　　　( D ) TOPOLOGY: linear ( i x ) FEATURE:
　　　　　　( D ) OTHER INFORMATION: All C'S are 2'-NH2 cytosine ( i x ) FEATURE:
　　　　　　( D ) OTHER INFORMATION: All U'S are 2'-NH2 uracil ( x i ) SEQUENCE DESCRIPTION: SEQ ID NO:119:

GGGAGACAAG AAUAACGCUC AAUAGGGCAG AGGGAGUGGU UAGGGCUGUG　　　　50

AUUUCGACAG GAGGCUCACA ACAGGC　　　　76

( 2 ) INFORMATION FOR SEQ ID NO:120:

( i ) SEQUENCE CHARACTERISTICS:
　　　　　　( A ) LENGTH: 76 base pairs
　　　　　　( B ) TYPE: nucleic acid
　　　　　　( C ) STRANDEDNESS: single (D) TOPOLOGY: linear (ix) FEATURE:
    (D) OTHER INFORMATION: All C'S are 2'-NH2 cytosine (ix) FEATURE:
    (D) OTHER INFORMATION: All U'S are 2'-NH2 uracil (xi) SEQUENCE DESCRIPTION: SEQ ID NO:120:

GGGAGACAAG AAUAACGCUC AAGGGUAGUG GGAAGGGUAA GGGCCGAGGU                50

GGUUCGACAG GAGGCUCACA ACAGGC                                          76

(2) INFORMATION FOR SEQ ID NO:121:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO:121:

GGGAGACAAG AAUAACGCUC AAAAUACACA CCGCGGGAAG GGAGGGUGGA                50

AAUUCGACAG GAGGCUCACA ACAGGC                                          76

(2) INFORMATION FOR SEQ ID NO:122:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO:122:

GGGAGACAAG AAUAACGCUC AAAGACUACA GCGCGGGUUA GGGUUGAGGG                50

AAUUCGACAG GAGGCUCACA ACAGGC                                          76

(2) INFORMATION FOR SEQ ID NO:123:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C'S are 2'-NH2 cytosine (ix) FEATURE:
        (D) OTHER INFORMATION: All U'S are 2'-NH2 uracil (xi) SEQUENCE DESCRIPTION: SEQ ID NO:123:

GGGAGACAAG AAUAACGCUC AAUACGAGCA AGCGGGCGAA GGGUUGAGGG                50

AAUUCGACAG GAGGCUCACA ACAGGC                                          76

(2) INFORMATION FOR SEQ ID NO:124:

( i ) SEQUENCE CHARACTERISTICS:
  ( A ) LENGTH: 76 base pairs
  ( B ) TYPE: nucleic acid
  ( C ) STRANDEDNESS: single
  ( D ) TOPOLOGY: linear ( i x ) FEATURE:
  ( D ) OTHER INFORMATION: All C'S are 2'-NH2 cytosine ( i x ) FEATURE:
  ( D ) OTHER INFORMATION: All U'S are 2'-NH2 uracil ( x i ) SEQUENCE DESCRIPTION: SEQ ID NO:124:

GGGAGACAAG AAUAACGCUC AACAAGGUGG UGGAGGAGGA UACGAUCUGC     50

AGUUCGACAG GAGGCUCACA ACAGGC     76

( 2 ) INFORMATION FOR SEQ ID NO:125:

( i ) SEQUENCE CHARACTERISTICS:
    ( A ) LENGTH: 75 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH2 cytosine ( i x ) FEATURE:
    ( D ) OTHER INFORMATION: All U'S are 2'-NH2 uracil ( x i ) SEQUENCE DESCRIPTION: SEQ ID NO:125:

GGGAGACAAG AAUAACGCUC AAGGAGGGAA GGAGGGCAGG UGAUGGGUCA     50

GUUCGACAGG AGGCUCACAA CAGGC     75

( 2 ) INFORMATION FOR SEQ ID NO:126:

( i ) SEQUENCE CHARACTERISTICS:
    ( A ) LENGTH: 76 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH2 cytosine ( i x ) FEATURE:
    ( D ) OTHER INFORMATION: All U'S are 2'-NH2 uracil ( x i ) SEQUENCE DESCRIPTION: SEQ ID NO:126:

GGGAGACAAG AAUAACGCUC AAUGAUGGCG GUAGUGGAGG UAAUGAGCGU     50

GAUUCGACAG GAGGCUCACA ACAGGC     76

( 2 ) INFORMATION FOR SEQ ID NO:127:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C'S are 2'-NH2 cytosine ( i x ) FEATURE:
    ( D ) OTHER INFORMATION: All U'S are 2'-NH2 uracil ( x i ) SEQUENCE DESCRIPTION: SEQ ID NO:127:

GGGAGACAAG AAUAACGCUC AAGCAACUGG GGGCGGGUGG UGUGAGGAUU     50

CGACAGGAGG CUCACAACAG GC     72

( 2 ) INFORMATION FOR SEQ ID NO:128:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:128:

GGGAGACAAG AAUAACGCUC AAGGAGGGGC CUAUAGGGGU GGUGGUGUAC     50

GAUUCGACAG GAGGCUCACA ACAGGC     76

( 2 ) INFORMATION FOR SEQ ID NO:129:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:129:

GGGAGACAAG AAUAACGCUC AAUAUAGGGU AGUGGGUGUA GGUAGGGCGA     50

CAUUCGACAG GAGGCUCACA ACAGGC     76

( 2 ) INFORMATION FOR SEQ ID NO:130:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:130:

GGGAGACAAG AAUAACGCUC AAGAGGGUUG GAGGGCAUGG GGCAGGAACC     50

GGUUCGACAG GAGGCUCACA ACAGGC     76

( 2 ) INFORMATION FOR SEQ ID NO:131:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:131:

```
GGGAGACAAG  AAUAACGCUC  AACGUAGAAC  UGGCGGGCAG  UGGGGGGGAU                    50

GCUUCGACAG  GAGGCUCACA  ACAGGC                                                76
```

( 2 ) INFORMATION FOR SEQ ID NO:132:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:132:

```
GGGAGACAAG  AAUAACGCUC  AAUGAGGGGA  CGAGGGAUGU  GGGGAGCGGG                    50

ACUUCGACAG  GAGGCUCACA  ACAGGC                                                76
```

( 2 ) INFORMATION FOR SEQ ID NO:133:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:133:

```
GGGAGACAAG  AAUAACGCUC  AACGAGGGAU  GGGAGGCGUG  UGGAAGAUGC                    50

AAUUCGACAG  GAGGCUCACA  ACAGGC                                                76
```

( 2 ) INFORMATION FOR SEQ ID NO:134:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:134:

```
GGGAGACAAG  AAUAACGCUC  AAGCAUCCGG  GGACAAGAUG  GGUCGGUAAG                    50

GUUUCGACAG  GAGGCUCACA  ACAGGC                                                76
```

( 2 ) INFORMATION FOR SEQ ID NO:135:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
    ( D ) OTHER INFORMATION: All U'S are 2'-NH2 uracil ( x i ) SEQUENCE DESCRIPTION: SEQ ID NO:135:

GGGAGACAAG AAUAACGCUC AAGUGUGCGG GGUCAAGACG GGUGGCGUGC                50

GUUCGACAGG AGGCUCACAA CAGGC                                          75

( 2 ) INFORMATION FOR SEQ ID NO:136:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:136:

GGGAGACAAG AAUAACGCUC AAUCAAACCA UGGGGCGGGU GGUACGAGGA                50

ACUUCGACAG GAGGCUCACA ACAGGC                                         76

( 2 ) INFORMATION FOR SEQ ID NO:137:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:137:

GGGAGACAAG AAUAACGCUC AACGAGUCCG AGGGAUGGGU GGUGUGCGGC                50

AAUUCGACAG GAGGCUCACA ACAGGC                                         76

( 2 ) INFORMATION FOR SEQ ID NO:138:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:138:

GGGAGACAAG AAUAACGCUC AACAGUGUCG GAGAGGAGGA UGGAGGUAUG                50

AAUUCGACAG GAGGCUCACA ACAGGC                                         76

( 2 ) INFORMATION FOR SEQ ID NO:139:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
    ( D ) OTHER INFORMATION: All C'S are 2'-NH2 cytosine ( i x ) FEATURE:
    ( D ) OTHER INFORMATION: All U'S are 2'-NH2 uracil ( x i ) SEQUENCE DESCRIPTION: SEQ ID NO:139:

GGGAGGACGA UGCGGCACCA CUACGCGGGA AGGGUAGGGU GGAUUACAAG    50

GUGUGACCGC UCCGUCAGAC GACTCGCCCG A    81

( 2 ) INFORMATION FOR SEQ ID NO:140:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:140:

GGGAGGACGA UGCGGUACGG UUAACGGGGG UGGUGUGGGA GGACACAAAG    50

CGCGUACCUG CCCCCAGACG ACTCGCCCGA    80

( 2 ) INFORMATION FOR SEQ ID NO:141:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:141:

GGGAGGACGA UGCGGAGGUC CUCGAGGGUC UGGGUGUGGG AGUGGGCAUG    50

GACCAAUACC GCGUGCAGAC GACTCGCCCG A    81

( 2 ) INFORMATION FOR SEQ ID NO:142:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C'S are 2'-NH2 cytosine ( i x ) FEATURE:
        ( D ) OTHER INFORMATION: All U'S are 2'-NH2 uracil ( x i ) SEQUENCE DESCRIPTION: SEQ ID NO:142:

GGGAGGACGA UGCGGAAACC CAUCCUGCGC GGGAUGGGAG GGUGGAAACA    50

CUAGAGCUUC GCCUGCAGAC GACTCGCCCG A    81

( 2 ) INFORMATION FOR SEQ ID NO:143:

( i ) SEQUENCE CHARACTERISTICS:

( A ) LENGTH: 81 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH2 cytosine ( i x ) FEATURE:
( D ) OTHER INFORMATION: All U'S are 2'-NH2 uracil ( x i ) SEQUENCE DESCRIPTION: SEQ ID NO:143:

GGGAGGACGA UGCGGAACUG GUGGUCACGC GUUGAGGUGG UGGAGGUGGA         50

UUCAACGGUC GAGGGCAGAC GACTCGCCCG A                             81

( 2 ) INFORMATION FOR SEQ ID NO:144:

( i ) SEQUENCE CHARACTERISTICS:
( A ) LENGTH: 81 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH2 cytosine ( i x ) FEATURE:
( D ) OTHER INFORMATION: All U'S are 2'-NH2 uracil ( x i ) SEQUENCE DESCRIPTION: SEQ ID NO:144:

GGGAGGACGA UGCGGCAUGA AAGUAGGGUU AUGAAGGCGG UAGAUGGAGG         50

AGGUUGGGUU GCCGCCAGAC GACTCGCCCG A                             81

( 2 ) INFORMATION FOR SEQ ID NO:145:

( i ) SEQUENCE CHARACTERISTICS:
( A ) LENGTH: 81 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH2 cytosine ( i x ) FEATURE:
( D ) OTHER INFORMATION: All U'S are 2'-NH2 uracil ( x i ) SEQUENCE DESCRIPTION: SEQ ID NO:145:

GGGAGGACGA UGCGGGUCUA UUGGGUAGGU GUUUGCAAGA AUUCCGCACG         50

AUAGGUAAAA CAGUGCAGAC GACTCGCCCG A                             81

( 2 ) INFORMATION FOR SEQ ID NO:146:

( i ) SEQUENCE CHARACTERISTICS:
( A ) LENGTH: 80 base pairs
( B ) TYPE: nucleic acid
( C ) STRANDEDNESS: single
( D ) TOPOLOGY: linear ( i x ) FEATURE:
( D ) OTHER INFORMATION: All C'S are 2'-NH2 cytosine ( i x ) FEATURE:
( D ) OTHER INFORMATION: All U'S are 2'-NH2 uracil ( x i ) SEQUENCE DESCRIPTION: SEQ ID NO:146:

GGGAGGACGA UGCGGUGUAG GGGAAGUACG AGAGUGGGAG CGGCCGUAUA         50

GGUGGGAGUG UGCUCAGACG ACTCGCCCGA                               80

HIGH-AFFINITY OLIGONUCLEOTIDE LIGANDS TO VASCULAR ENDOTHELIAL GROWTH FACTOR (VEGF)

RELATED APPLICATIONS

This application is a Continuation-in-Part of U.S. patent application Ser. No. 07/714,131, filed Jun. 10, 1991, entitled Nucleic Acid Ligands, now U.S. Pat. No. 5,475,096, which is a Continuation-in-Part of U.S. patent application Ser. No. 07/536,428, filed Jun. 11, 1990, entitled Systematic Evolution of Ligands by Exponential Enrichment, now abandoned, and U.S. patent application Ser. No. 07/964,624, filed Oct. 21, 1992 entitled Nucleic Acid Ligands to HIV-RT and HIV-1 Rev, now U.S. Pat. No. 5,496,938.

FIELD OF THE INVENTION

Described herein are high affinity nucleic acid ligands to vascular endothelial growth factor (VEGF). The method utilized herein for identifying such nucleic acid ligands is called SELEX, an acronym for Systematic Evolution of Ligands by EXponential enrichment.

BACKGROUND OF THE INVENTION

Neovascularization or angiogenesis is the process in which sprouting new blood vessels are formed from the existing endothelium in response to external stimuli that signal inadequate blood supply. Angiogenesis is generally rare under normal physiological conditions but frequently accompanies certain pathological conditions such as psoriasis, rheumatoid arthritis, hemangioma, and solid tumor growth and metastasis (Folkman & Klagsbrun, 1987) Science 235, 442–447; Kim et al., (1993) Nature 362, 841–844). Several growth factors that are capable of inducing angiogenesis in vivo have been identified to date including basic and acidic fibroblast growth factors (aFGF, bFGF), transforming growth factors α and β (TGFα, TGFβ), platelet derived growth factor (PDGF), angiogenin, platelet-derived endothelial cell growth factor (PD-ECGF), interleukin-8 (IL-8), and vascular endothelial growth factor (VEGF).

VEGF was originally purified from guinea pig ascites and tumor cell cultures as a factor that increases vascular permeability (Senger, D. R. et al. (1983), Science 219:983–985) and it has therefore also been referred to as vascular permeability factor (VPF). VEGF is a heat and acid-stable, disulfide-linked homodimer. Four isoforms have been described (121, 165, 189 and 206 amino acids, respectively) and are believed to be the result of alternative splicing of mRNA. Despite the presence of an identical N-terminal hydrophobic signal sequence in all molecular isoforms of VEGF, only the two lower molecular weight species are efficiently secreted (Ferrara, N. et al. (1991) J. Cell. Biochem. 47:211–218). The predominant VEGF isoform in most cells and tissues is the 165 amino acid species. Although VEGF is typically glycosylated, glycosylation is only required for efficient secretion but not for activity (Yeo, T-. K. et al. (1991) Biochem. Biophys. Res. Commun. 179:1568–1575; Peretz, D. et al. (1992) Biochem. Biophys. Res. Commun. 182:1340–1347). The amino acid sequence of VEGF is highly conserved across species and exhibits a modest but significant homology (18–20%) to PDGF A and B (Jakeman L. B. et al. (1992) J. Clin. Invest. 89:244–253; Ferrara et al. (1992) Endocrine Rev. 13:18–32).

Unlike other angiogenic growth factors, target cell specificity of VEGF is limited to vascular endothelial cells. The biological actions of VEGF are mediated through its interaction with specific cell-associated receptors which have been identified in the majority of tissues and organs (Jakeman, L. B. (1992) J. Clin. Invest. 89,244–253). Three high-affinity receptors for VEGF have been cloned to date: flt1, kdr/flk-1 and flt4 (Vaisman, N. et al. (1990) J. Biol. Chem. 265, 19461–19466; de Vries, C. et al. (1992) Science 255, 989–991; Galland, F. et al. (1993) Oncogene 8, 1233–1240). These receptors belong to a family of transmembrane tyrosine kinases and bind VEGF with dissociation constants between $10^{-11}$M to $10^{-12}$M. Recent experiments have shown that binding of VEGF to its high-affinity receptors is significantly enhanced by heparin or cell surface-associated heparin-like molecules (Gitay-Goren, H. (1992) J. Biol. Chem. 267:6093–6098).

In addition to promoting the growth of vascular endothelial cells and inducing vascular leakage, VEGF is also known to induce the proteolytic enzymes interstitial collagenase, urokinase-type plasminogen activator (uPA) and tissue-type plasminogen activator (tPA) (Unemori E. et al. (1993) J. Biol. Chem. 153:557; Pepper, M. S. et al. (1992) Biochem. Biophys. Res. Commun. 189:824). These enzymes are known to play a prominent role in angiogenesis-related extracellular matrix degradation.

As a secreted and specific mitogen for endothelial cells, VEGF may be one of the major angiogenesis inducers in vivo. Several recent observations have supported this notion. For example, the expression of VEGF and its receptors accompanies angiogenesis associated with (i) embryonic development (Breier, G. et al. (1992) Development 114:521–532), (ii) hormonally-regulated reproductive cycle and (iii) tumor growth (Dvorak, H. F. (1991) J. Exp. Med. 174, 1275–1278; Shweiki, D. et al. (1992) Nature 359:843–845; Plate, K. H. et al. (1992) Nature 359:845–848). It is relevant to note that aggressive tumor growth is accompanied by the generation of necrotic areas where oxygen and nutrient supplies are inadequate. Oxygen deprivation (hypoxia) in tissues is a known angiogenesis stimulant. Interestingly, VEGF expression was found to be the highest in tumor cells facing the necrotic areas (Shweiki, D. et al. (1992) supra; Plate, K. H. et al. (1992) supra). It has therefore been suggested by these authors that VEGF plays a key role in hypoxia-induced angiogenesis.

Recent experiments with neutralizing monoclonal antibodies (MAbs) to VEGF have been especially meaningful for establishing that this growth factor is an important tumor angiogenesis inducer in vivo (Kim, K. J. et al. (1993) Nature 362:841–844). Immunocompromised (nude) mice injected with human rhabdomyosarcoma, glioblastoma or leiomyosarcoma cell lines rapidly develop tumors. Specific neutralizing MAb to VEGF were found to inhibit the growth of these tumors. The density of tumor vasculature was decreased in MAb-treated animals as compared to controls. The same MAb, on the other hand, had no effect on the growth rate of the tumor cells in vitro suggesting that the growth inhibition was not mediated at the cellular level and appears to be mediated by the 165-amino acid isoform of VEGF.

BRIEF SUMMARY OF THE INVENTION

Herein described is the isolation and characterization of binding properties of a set of high-affinity RNA ligands to VEGF. These ligands were selected from an initial pool of about $10^{14}$ RNA molecules randomized at thirty contiguous positions. The evolved RNA ligands bind VEGF with affinities in the low nanomolar range.

Also included herein are modified RNA ligands to VEGF. Such modified RNA ligands may be prepared after the identification of 2'-OH RNA ligands or by performing SELEX using a candidate mixture of modified RNAs. For example, 2'-NH$_2$ pyrimidine RNA ligands to VEGF are described herein.

The present invention includes the method of identifying nucleic acid ligands and ligand sequences to VEGF comprising:

a) contacting a candidate mixture of nucleic acids with VEGF, wherein nucleic acids having an increased affinity to VEGF relative to the candidate mixture may be partitioned from the remainder of the candidate mixture;

b) partitioning the increased affinity nucleic acids from the remainder of the candidate mixture, and c) amplifying the increased affinity nucleic acids, whereby nucleic acid ligands to VEGF may be identified.

BRIEF DESCRIPTION OF THE FIGURES

FIG. 1 shows the starting RNA and PCR primers used in the SELEX experiment described in Examples 1 and 2.

FIGS. 2A–F show the aligned sequences and predicted secondary structures for the six families (grouped by primary sequence homology) of RNA ligands to VEGF. Arrows underline the inverted repeats of the double stranded (stem) regions. Lowercase and uppercase letters are used to distinguish nucleotides in the constant and the evolved sequence regions, respectively. Positions are numbered consecutively starting (arbitrarily) with the evolved nucleotide closest to the 5' end of the shown window.

FIG. 8 shows the starting random RNAs for experiments A and B, and PCR primers used in identifying 2'-NH$_2$-RNA ligands to VEGF (Example 4).

FIGS. 9A–G show 2'-NH$_2$-RNA ligands to VEGF identified via the SELEX technology as described in Example 4.

DETAILED DESCRIPTION OF THE INVENTION

Figure 3C:
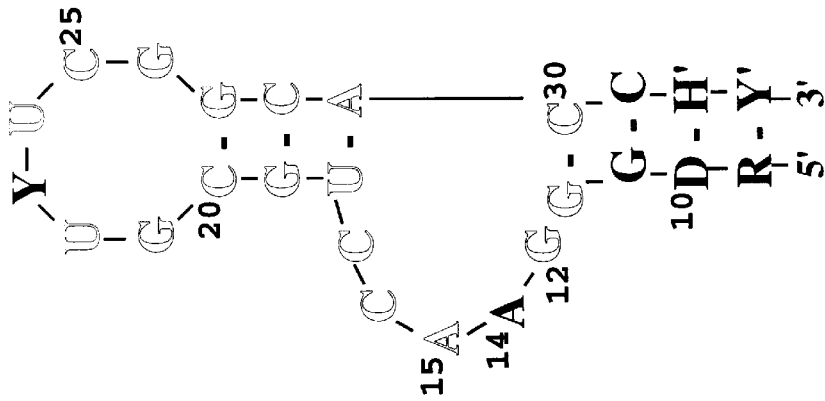
FIGS. 3A–F show the consensus sequences and predicted secondary structures for certain of the VEGF ligand families. Plain text is used to designate positions that occur at >60% but <80% frequencies. Positions where individual nucleotides are strongly conserved (frequencies>80%) are outlined. Residues in parenthesis occur at that position with equal frequencies to gaps. The numbering system described in the legend to FIG. 2 is used. R=A or G; Y=C or U; M=A or C; D=A, G or U; V=G, A or C; S=G or C; K=G or U; N=any base and prime (') indicates a complementary base.

This application describes high-affinity nucleic acid ligands to vascular endothelial growth factor (VEGF) identified through the method known as SELEX. The SELEX method is described in detail in U.S. patent application Ser. No. 07/536,428, filed Jun. 11, 1990, entitled Systematic Evolution of Ligands by Exponential Enrichment, now abandoned, U.S. patent application Ser. No. 07/714,131, filed Jun. 10, 1991, entitled Nucleic Acid Ligands, now U.S. Pat. No. 5,475,096, U.S. patent application Ser. No. 07/931, 473, filed Aug. 17, 1992, entitled Methods for Identifying Nucleic Acid Ligands, now U.S. Pat. No. 5,270,163.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets where the protein is and is not a nucleic acid binding protein.

SELEX provides high affinity ligands of a target molecule. This represents a singular achievement that is unprecedented in the field of nucleic acids research. The present invention applies the SELEX procedure to the specific target of vascular endothelial growth factor (VEGF). In the Example section below, the experimental parameters used to isolate and identify the nucleic acid ligand solutions to VEGF are described.

In order to produce nucleic acids desirable for use as a pharmaceutical, it is preferred that the nucleic acid ligand 1) binds to the target in a manner capable of achieving the desired effect on the target; 2) be as small as possible to obtain the desired effect; 3) be as stable as possible; and 4) be a specific ligand to the chosen target. In most situations it is preferred that the nucleic acid ligand have the highest possible affinity to the target.

In co-pending and commonly assigned U.S. patent application Ser. No. 07/964,624, filed Oct. 21, 1992 ('624), now U.S. Pat. No. 5,496,938, methods are described for obtaining improved nucleic acid ligands after SELEX has been performed. The '624 application, entitled Nucleic Acid Ligands to HIV-RT and HIV-1 Rev is specifically incorporated herein by reference.

This invention includes the specific RNA ligands to VEGF shown in FIGS. 2A–F (SEQ ID NOS:4–38). The scope of the ligands covered by this invention extends to all RNA ligands of VEGF identified according to the SELEX procedure. More specifically, this invention includes nucleic acid sequences that are substantially homologous to and that have substantially the same ability to bind VEGF as the specific nucleic acid ligands shown in FIGS. 2A–F. By substantially homologous it is meant a degree of primary sequence homology in excess of 70%, most preferably in excess of 80%. Substantially the same ability to bind VEGF means that the affinity is within one order of magnitude of the affinity of the ligands described herein. It is well within the skill of those of ordinary skill in the art to determine whether a given sequence—substantially homologous to those specifically described herein—has substantially the same ability to bind VEGF.

This invention also includes the 2'-$NH_2$ modified RNA ligands to VEGF as shown in FIGS. 9A–G (SEQ ID NOS:63–146). The scope of the present invention extends, therefore, to all modified nucleic acid ligands identified according to the SELEX method as well as to all sequences that are substantially homologous to and that have substantially the same ability to bind VEGF as ligands predicted in FIGS. 9A–G.

This invention encompasses the use of the disclosed ligands to identify a second ligand. In one embodiment, a first SELEX identified ligand which binds to a specific site of the target molecule is used to elute secondary ligands binding to the same site. In another embodiment, a first SELEX identified ligand binding to a specific site of the target molecule is used to select secondary ligands which do not bind to the same site. In this case, SELEX is conducted in the presence of the first ligand such that the binding site is saturated with the first ligand and selection occurs for ligands binding elsewhere on the target molecule. In a further embodiment analogous to the generation of anti-idiotype antibodies, a SELEX identified ligand to VEGF may itself be used as a target molecule to identify secondary ligands resembling the VEGF binding site. Such secondary ligands may compete with VEGF-substrate binding and inhibit the biological activity of VEGF.

A review of the sequence homologies of the RNA ligands of VEGF shown in FIGS. 2A–F and 9A–G shows that sequences with little or no primary homology may have substantially the same ability to bind VEGF. For these reasons, this invention also includes nucleic acid ligands that have substantially the same structure as the ligands presented herein and the substantially the same ability to bind VEGF as the nucleic acid ligands shown in FIGS. 2A–F and 9A–G.

The following examples are provided to explain and illustrate the present invention and are not to be taken as limiting of the invention.

Example 1 describes the experimental procedures used to generate high-affinity nucleic acid ligands to VEGF. Example 2 describes the high-affinity RNA ligands to VEGF shown in FIGS. 2A–F. Example 3 describes the specificity of truncated RNA ligands to VEGF. Example 4 describes the experimental procedures used to generate 2'-$NH_2$ pyrimidine modified RNA ligands to VEGF.

EXAMPLE 1

Experimental Procedures

Materials. Recombinant human VEGF (165 amino acid form; MW 46,000) was a generous gift from Dr. Napoleone Ferrara (Genentech). All other reagents and chemicals were of the highest purity available and were purchased from commercial sources.

SELEX. Essential features of the SELEX protocol have been described in detail in U.S. Pat. No. 5,270,163 as well as in previous papers from these laboratories (See, e.g., Schneider et al. (1992) J. Mol. Biol. 228:862). Briefly, DNA templates for in vitro transcription (that contain a region of thirty random positions flanked by constant sequence regions) and the corresponding PCR primers were prepared chemically using established solid phase oligonucleotide synthesis protocols.

The random region was generated by utilizing an equimolar mixture of the four unmodified nucleotides during oligonucleotide synthesis. The two constant regions were designed to contain PCR primer annealing sites, primer annealing site for cDNA synthesis, T7 RNA polymerase promoter region and restriction enzyme sites that allow cloning into vectors (FIG. 1) SEQ ID NOS:1–3). An initial pool of RNA molecules was prepared by in vitro transcription of approximately 200 picomoles ($10^{14}$ molecules) of the double stranded DNA template utilizing T7 RNA polymerase. Transcription mixtures consisting of 100–300 nM template, 5 units/$\mu$l T7 RNA polymerase, 40 mM Tris-Cl buffer (pH 8.0) containing 12 mM $MgCl_2$, 5 mM DTT, 1 mM spermidine, 0.002% Triton X-100, 4% PEG were incubated at 37° C. for 2–3 hours. These conditions typically resulted in transcriptional amplification of 10 to 100-fold. Selections for high affinity RNA ligands were done by incubating VEGF with RNA for 10–20 minutes at 37° C. in 50 ml of phosphate buffered saline (PBS=10.1 mM $Na_2HPO_4$, 1.8 mM $KH_2PO_4$, 137 mM NaCl, 2.7 mM KCl, pH 7.4) and then separating the protein-RNA complexes from the unbound species by nitrocellulose filter partitioning (Tuerk, C. and Gold, L. (1990) Science 249, 505–510). The selected RNA (which typically amounted to 5–10% of the total input RNA) was then extracted from the filters and reverse transcribed into cDNA by avian myeloblastoma virus reverse transcriptase (AMV RT). Reverse transcriptions were done at 48° C. (60 min) in 50 mM Tris buffer (pH 8.3), 60 mM NaCl, 6 mM Mg(OAc)$_2$, 10 mM DTT and 1 unit/$\mu$l AMV RT. Amplification of the cDNA by PCR under standard conditions yielded a sufficient amount of double-stranded DNA for the next round of in vitro transcription.

Nitrocellulose Filter Binding Assays. Oligonucleotides bound to proteins can be effectively separated from the unbound species by filtration through nitrocellulose membrane filters (Yarus, M. and Berg, P. (1970) Anal. Biochem. 35:450–465; Lowary, P. T. and Uhlenbeck, O. C. (1987) Nucleic Acids Res. 15:10483–10493; Tuerk, C. and Gold, L. (1990) supra). Nitrocellulose filters (0.2 $\mu$m pore size, Schleicher and Schuell, Keene, NH) were secured on a filter manifold and washed with 4–10 ml of buffer. Following incubations of $^{32}P$ labeled RNA with serial dilutions of the protein for 10 min at 37° C. in buffer (PBS) containing 0.01% human serum albumin (HSA), the solutions were applied to the filters under gentle vacuum in 45 ml aliquots and washed with 5 ml of PBS. The filters were then dried under an infrared lamp and counted in a scintillation counter.

Equilibrium Dissociation Constants. In the simplest case, equilibrium binding of RNA (R) to VEGF (P) can be described by eq. 1,

(1)

where Kd=([R][P]/[R.P]) is the equilibrium dissociation constant. Using the mass-balance equations, the fraction of bound RNA at equilibrium (q) can be expressed in terms of measurable quantities (eq. 2), $$q=(f/2Rt)\{Pt+Rt+Kd-[(Pt+Rt+Kd)^2-4PtRt]^{1/2}\} \quad (2)$$

where Pt and Rt are total protein and total RNA concentrations and f reflects the efficiency of retention of the protein-RNA complexes on nitrocellulose filters. The average value of f for VEGF in our assays was 0.7.

Most RNA ligands exhibited biphasic binding to VEGF. For those ligands, binding of RNA to VEGF is described by a model where total RNA is assumed to be partitioned between two non-interconverting components (R1 and R2) that bind to VEGF with different affinities (eqs 3 and 4).

(3)

(4)

In this case, the fraction of total bound RNA (q) is given by eq. 5.

$$q=(f/2Rt)\{2Pt+Rt+Kd1+Kd2-[(Pt+\chi1Rt+Kd1)^2-4Pt\chi1Rt]^{1/2}-[(Pt+\chi2Rt+Kd2)^2-4Pt\chi2Rt]^{1/2}\} \quad (5)$$

where $\chi1$ and $\chi2(=1-c1)$ are the mole fractions of R1 and R2 and Kd1 and Kd2 are the corresponding dissociation constants.

Internally-labeled RNA ligands used for binding studies were prepared by in vitro transcription using T7 RNA polymerase (Milligan et al. (1987) Nucl. Acids Res. 15:8783) and were purified on denaturing polyacrylamide gels to ensure size homogeneity. All RNA ligands were diluted to about 1 nM in PBS, denatured at 90° C. for 2 minutes, and then cooled on ice prior to incubation with the protein. This denaturation/renaturation cycle performed at high dilution is necessary to ensure that the RNA is essentially free from dimers and other higher order aggregates. Concentrations of the stock solutions of VEGF, from which other dilutions were made, were determined from the absorbance reading at 280 nm using the calculated value for $\epsilon_{280}$ of 46,600 $M^{-1}cm^{-1}$ for the VEGF dimer (Gill et al. (1989) Anal. Biochem. 182:319). Data sets that define the binding curves were fit to either eq. 2 or eq. 5 by the non-linear least squares method using the software package Kaleidagraph (Synergy Software, Reading, Pa.).

Information Boundary Determinations. High-affinity VEGF ligands were radiolabeled at the 5'-end with $\gamma$-$^{32}P$-ATP (New England Biolabs, Beverly, Mass.) and T4 polynucleotide kinase (New England Biolabs, Beverly, Mass.) for the 3'-boundary determinations, or at the 3'-end with $\alpha$-$^{32}PCp$ and T4 RNA ligase (New England Biolabs) for the 5'-boundary determination. Radiolabeled RNA ligands were subjected to partial alkaline hydrolysis and then selectively bound in solution to VEGF at 5, 0.5, or 0.125 nM before being passed through nitrocellulose filters. Retained oligonucleotides were resolved on 8% denaturing polyacrylamide gels. In each experiment, the smallest radiolabeled oligonucleotide bound by VEFG at the lowest protein concentration defines the information boundary. Partial digests of the 5'- or the 3'-labelled RNA ligands with RNAse $T_1$ (Boehringer Mannheim Biochemicals, Indianapolis, Ind.) were used to mark the positions of labeled oligonucleotides ending with a guanosine.

Cloning and Sequencing. Individual members of the enriched pool were cloned into pUC18 vector and sequenced as described (Schneider, D. et al. (1992) J. Mol. Biol. 228:862–869).

Receptor Binding. VEGF was radioiodinated by the Iodegen method (Jakeman et al. (1992) J. Clin. Invest. 89:244) to a specific activity of $2.4\times10^4$ cpm/ng. Human umbilical vein endothelial cells (HUVECs) were plated in 24-well plates at a density of $1-2\times10^5$ cells/well and grown to confluence in EGM (Clonetics, San Diego, Calif.) media (24–48 hrs). At confluence, the cells were washed 3 times with PBS and incubated for 2 hrs at 4° C. in α-MEM serum-free media containing $^{125}$I-labeled VEGF with or without unlabeled competitor (VEGF, EGF, or RNA). For experiments done with RNA, 0.2 units of placental RNase inhibitor (Promega, Madison, Wis.) were included in the media. It was determined that the RNA ligands were not degraded during the course of the experiment. At the end of the 2 hr incubation period, the supernatant was removed and the wells washed 2 times with PBS. HUVECs were then lysed with 1% triton X-100/1M NaOH and the amount of cell-associated $^{125}$I-VEGF determined by gamma counting.

EXAMPLE 2

RNA Ligands to VEGF.

Approximately $10^{14}$ RNA molecules randomized at thirty contiguous positions were used in the initial selection targeting VEGF. Random RNA bound to VEGF with an affinity of approximately 0.2 μM. After 13 rounds of SELEX, the observed improvement in affinity of the evolved RNA pool was about two orders of magnitude (data not shown). 64 isolates were cloned and sequenced from this evolved pool, and 37 unique sequences found (sequences differing at only one or two positions were not considered unique). 34 of the 37 unique sequences could be classified into six families based on sequence similarity in the evolved region (FIGS. 2A–F). Three unique clones, 4 (GGGAUGUUUGGCUAUCUCGGAUAGUGCCCC) (SEQ ID NO:39), 16 (GCUUAAUACGACUCACUNUAGGGAGCUCAG) (SEQ ID NO:40) and 18 (UUGAGUGAUGUGCUUGACGUAUCGCUGCAC) (SEQ ID NO:41) had a more limited sequence similarity with members of the six families.

Consensus Structures. In addition to allowing determination of consensus primary structures, groups of similar sequences consisting of members that share a defined functional property often contain useful clues for secondary structure prediction (James et al.(1989) Meth. Enzymol. 180:227). The underlying assumption is that ligands with similar primary structures are capable of adopting similar secondary structures in which the conserved residues are organized in unique, well-defined motifs. In this context, ligands which have strong, unambiguous secondary structures can provide good structural leads for other sequences within a similar set where consensus folding may be less obvious. Conserved elements of secondary structure, such as base-pairing, may also be detected through covariation analysis of aligned sequence sets (James et al. (1989) supra; Gutell et al. (1992) Nucl. Acids Res. 20:5785). The predicted consensus secondary structures for the six sequence families are shown in FIGS. 3A–F (SEQ ID NOS:42–47.

Figure 3B:
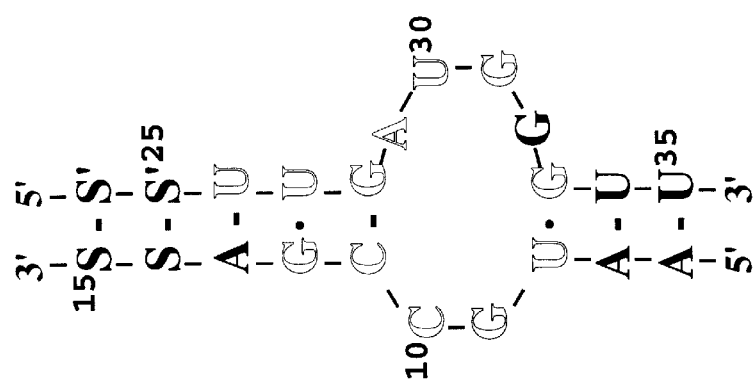
Figure 3A:
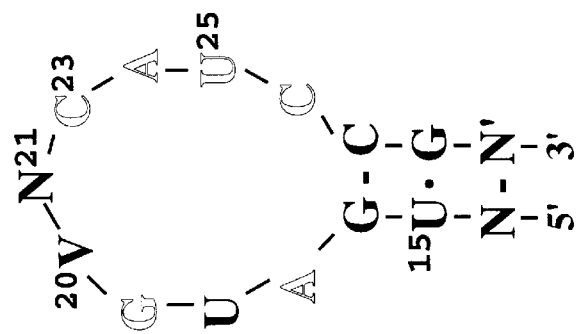
Figure 3F:
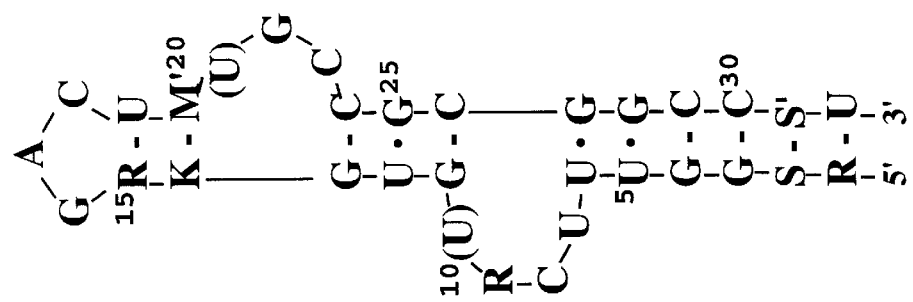
Figure 3E:
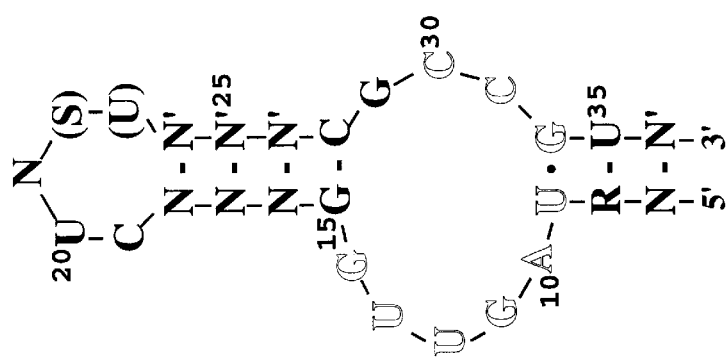
Figure 3D:
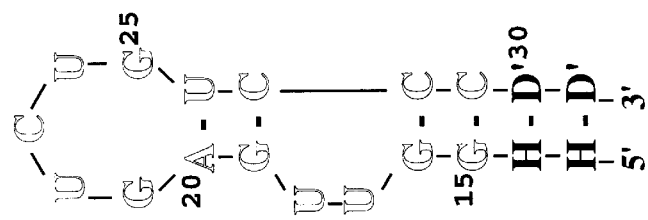
Figure 4A:
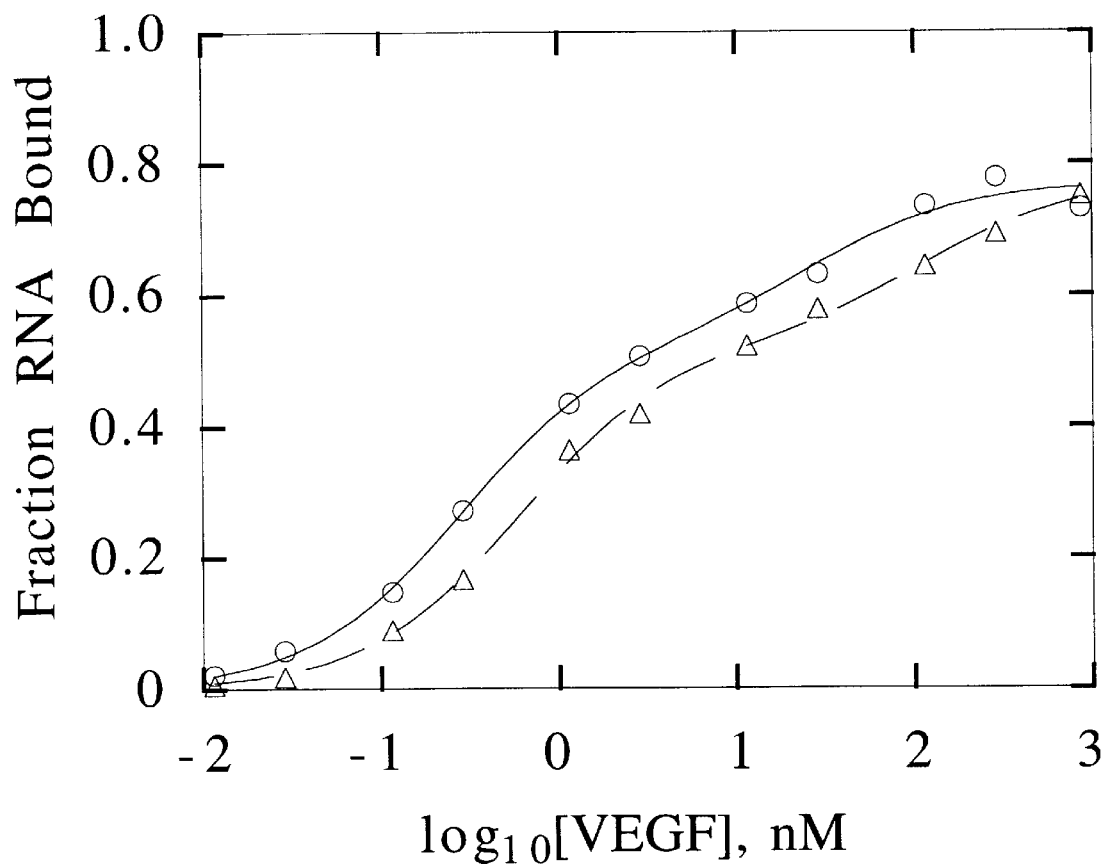
FIGS. 4A'F show the binding curves for a representative set of high-affinity ligands to VEGF. Full-length (o) and truncated (Δ) ligands tested were 100 (SEQ ID NO:11) and 100t (SEQ ID NO:51)(family 1, FIG. 4A), 44 (SEQ ID NO:20) and 44t (SEQ ID NO:52) (family 2, FIG. 4B), 12 (SEQ ID NO:22) and 12t (SEQ ID NO:53) (family 3, FIG. 4C), 40 (SEQ ID NO:28) and 40t (SEQ ID NO:54) (family 4, FIG. 4D), 84 (SEQ ID NO:36) and 84t SEQ ID NO:55) (family 5, FIG. 4E), and 126 (SEQ ID NO:38) and 126t (SEQ ID NO:56) (family 6, FIG. 4F). The fraction of $^{32}$P-labeled RNA bound to nitrocellulose filters is plotted as a function of total protein concentration and the lines represent the fit of the data points to eq. 2 (40t, 84 and 84t) or to eq. 5 (all other ligands). RNA concentrations were determined from their absorbance reading at 260 nm (and were typically <50 pM). Binding reactions were done at 37° C. in phosphate buffered saline containing 0.01% human serum albumin.
Figure 4B:
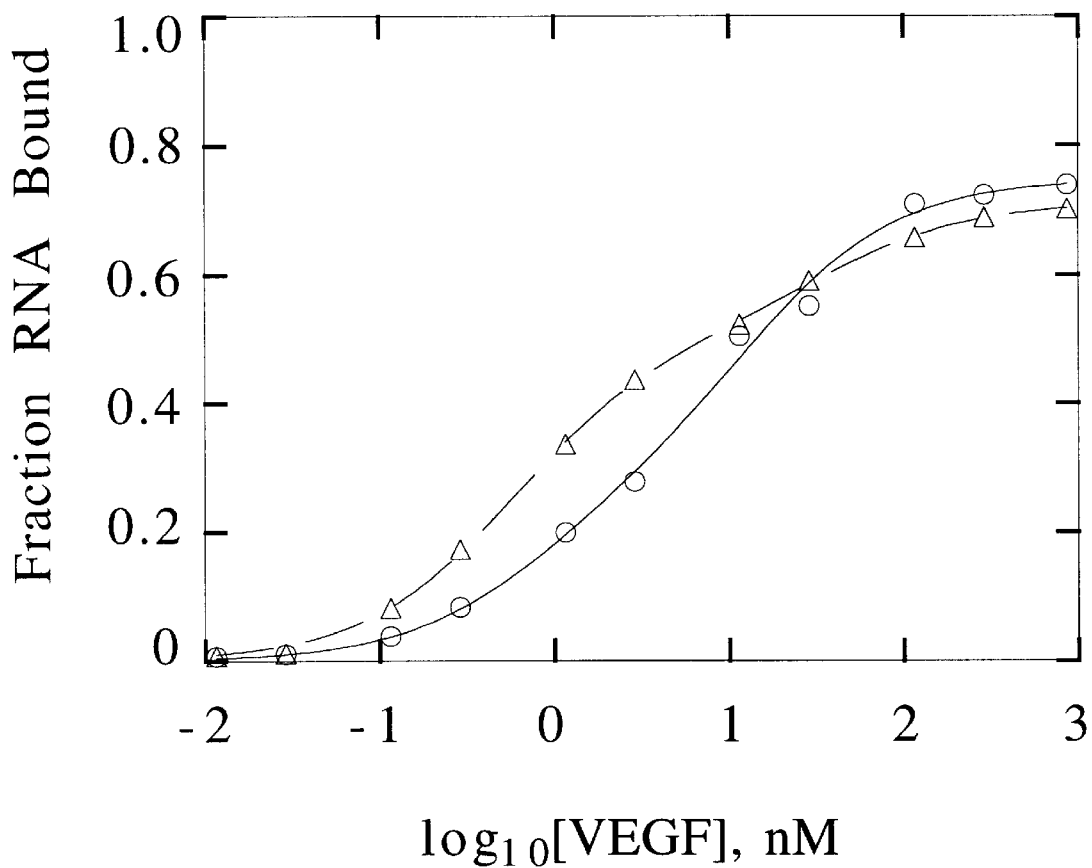
Figure 4C:
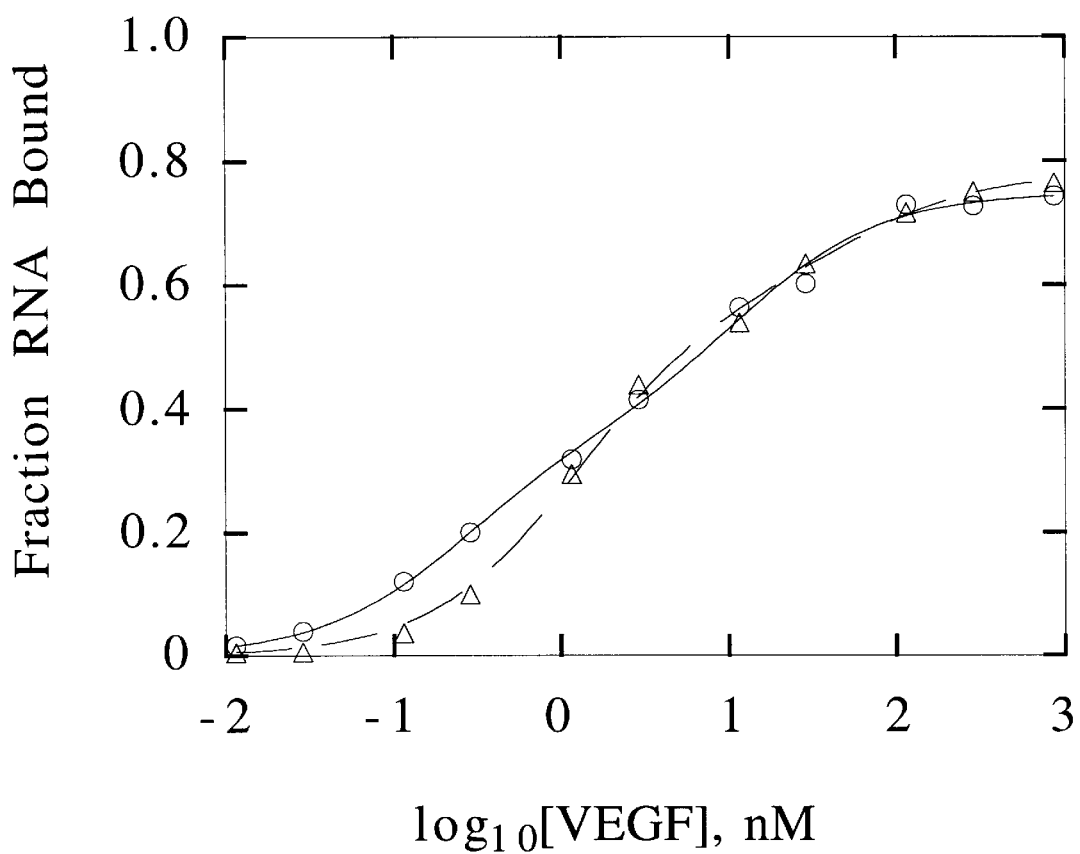
Figure 4D:
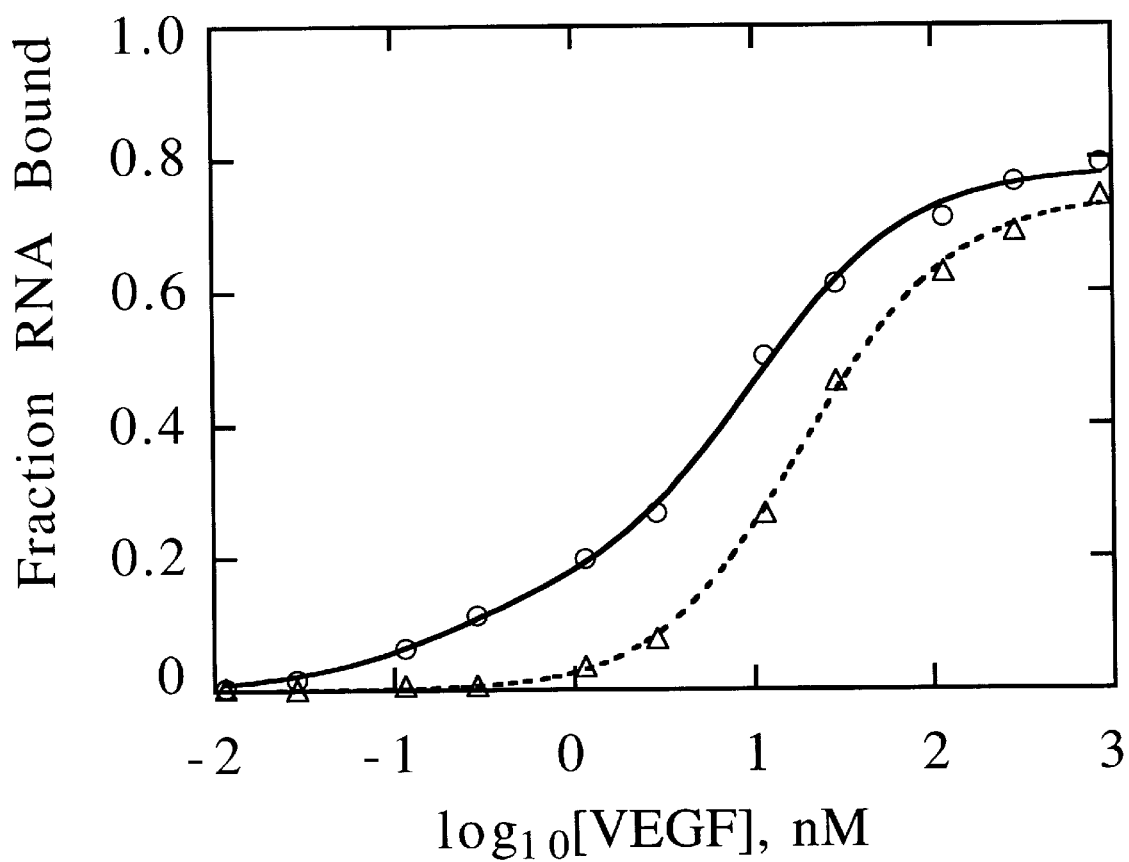
Figure 4E:
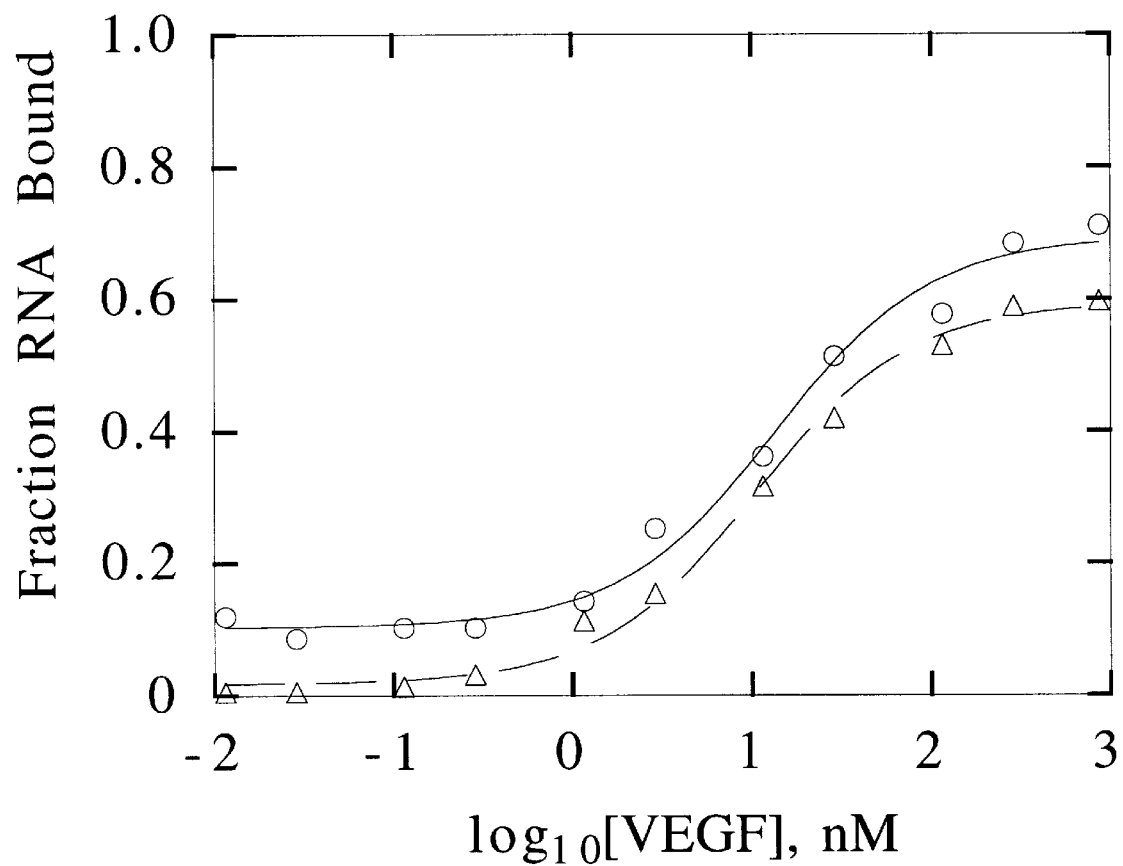
Figure 4F:
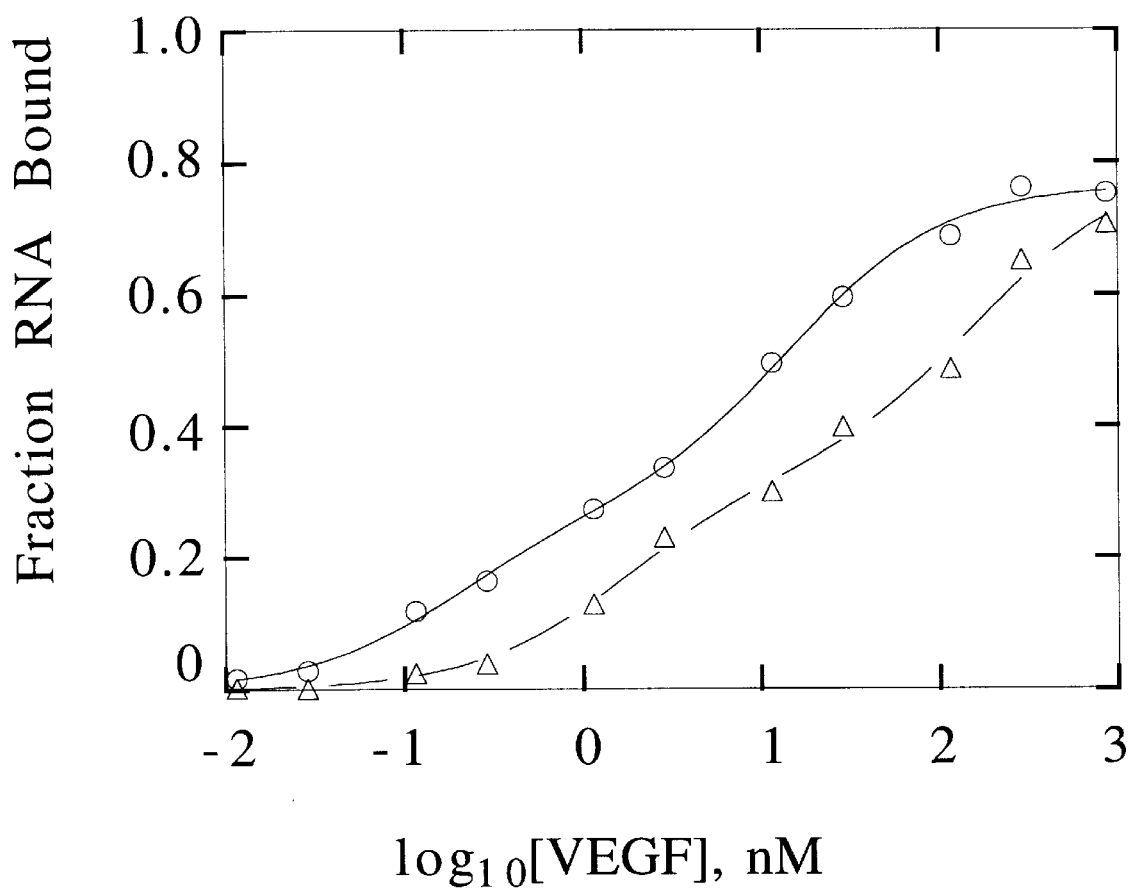

The most highly conserved residues in the family 1 sequence set (A17, G19 and the CAUC sequence at positions 23–26) can be accommodated in the 9–10 nucleotide loop FIG. 3A (SEQ ID NO:42). Base-pairing covariation between positions 16 and 27 (G-C occurs with a frequency of 8 out of 11 times (8/11) and C-G with a frequency of 3/11), positions 15 and 28 (U-G, 7/11; G-C, 3/11; U-A, 1/11) and positions 14 and 29 (G-C, 5/11; U-A, 2/11, and C-G, 1/11) supports the predicted secondary structure. It is worth noting that many ligands in this family have stable extended stems that contain up to 15 base pairs.

In the family 2 sequence set, the strongly conserved UGCCG and UUGAUG(G/U)G sequences (positions 8–12 and 26–33) are circularly permutated. In the consensus secondary structures, these nucleotides are found in an identical arrangement within or adjacent to the asymmetrical internal loop (FIG. 3B) (SEQ ID NO:43). This result suggests that the nucleotides outside of the consensus motif shown in FIG. 3B are unimportant for binding. Base-pairing covariation is noted between positions 5 and 36 (C-G, 2/7; G-C, 2/7; U-A, 1/7; G-U, 1/7), 6 and 35 (A-U, 4/7; C-G, 1/7; G-C, 1/7), 7 and 34 (A-U, 4/7; G-C, 1/7), 11 and 28 (C-G, 6/7; G-C, 1/7) , 12 and 27 (G-U, 6/7; C-G, 1/7), 13 and 26 (A-U, 5/7; G-C, 1/7; G-U, 1/7), 14 and 25 (G-C, 4/7; C-G, 2/7) and 15 and 24 (C-G, 4/7; G-C, 2/7).

Family 3 and family 4 sequence sets are characterized by highly conserved contiguous stretches of 21 (GGGAACCUGCGU(C/U)UCGGCACC (SEQ ID NO:48), positions 11–31) and 15 (GGUUGAGUCUGUCCC (SEQ ID NO:49), positions 15–29) arranged in bulged hairpin motifs (FIGS. 3C and D) (SEQ ID NOS:44–45). Base-pairing covariation is detected in family 3 between positions 8 and 33 (A-U, 2/4; G-C, 2/4), 9 and 32 (A-U, 2/4; U-A, 1/4; G-C, 1/4), and 10 and 31 (A-U, 1/4; G-C, 3/4) and in family 4 between positions 13 and 31 (A-U, 4/7; C-G, 2/7; U-A, 1/7) and 14 and 30 (C-G, 3/7; U-A, 3/7; A-U, 1/7).

Family 5 consensus secondary structure is an asymmetrical internal loop where the conserved UAGUUGG (positions 9–15) and CCG (positions 29–31) sequences are interrupted by less conserved sequences (FIG. 3E) (SEQ ID NO:46). Modest base-pairing covariation is found between positions 8 and 32 (A-U, 2/4; U-G, 1/4), 16 and 26 (G-C, 2/4; A-U, 1/4), 17 and 25 (A-U, 2/4; G-C, 1/4) and 18 and 24 (C-G, 2/4; G-C, 1/4).

Family 6 has only two sequences and therefore the concept of consensus sequence or consensus structure is less meaningful. Nevertheless, the two sequences are very similar (90% identity) and can be folded into a common motif (FIG. 3F) (SEQ ID NO:47). Base-pairing covariation is found between positions 1 and 32 (A-U, 1/2; G-U, 1/2), 2 and 31 (C-G, 1/2; G-C, 1/2), 14 and 20 (U-A, 1/2; G-C, 1/2) and 15 and 19 (A-U, 1/2; G-U, 1/2).

Affinities. The affinity of all unique sequence clones for VEGF was screened by determining the amount of RNA bound to VEGF at two protein concentrations (1 and 10 nM). Binding of the best ligands from each of the six sequence families was then analyzed over a range of protein concentrations (FIGS. 4A–F). Dissociation constants were calculated by fitting the data points to either eq. 2 (monophasic binding) or eq. 5 (biphasic binding) and their values are shown in Table 1.

Figures 5A, 5B:
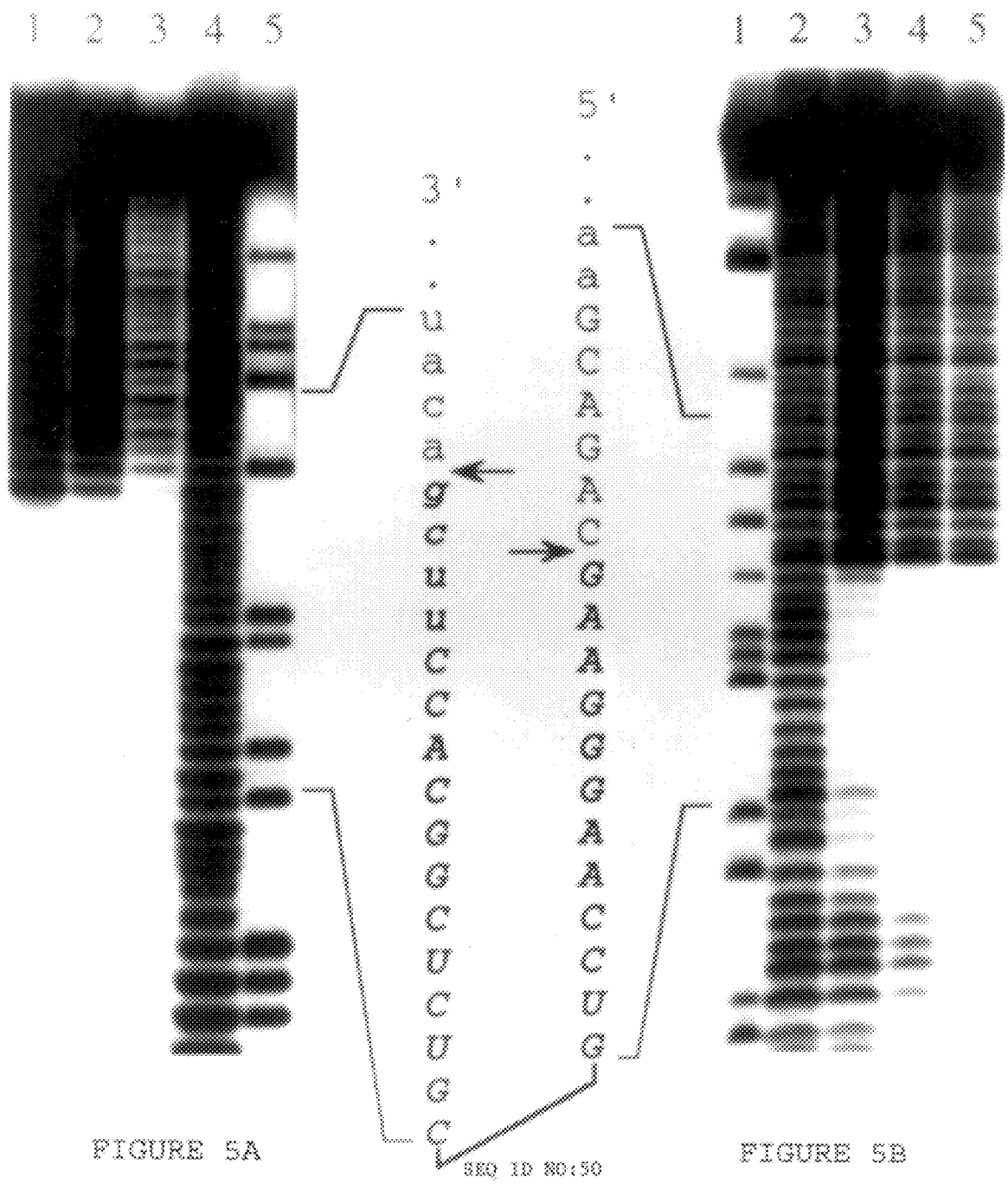
FIGS. 5A and B show the results of the determination of the 3'- and 5'-boundaries for a representative high-affinity VEGF ligand (ligand 12) (SEQ ID NO:50). The 3'-boundary determination (FIG. 5A) showing partially hydrolyzed 5'-end labeled RNA (lane 4), hydrolytic fragments retained on nitrocellulose filters following incubation of the partially hydrolyzed RNA with VEGF at 5 nM (lane 1), 0.5 nM (lane 2), or 0.125 nM (lane 3) and partial digest of the 5'-end labeled RNA with RNAse T$_1$ (lane 5) resolved on an 8% denaturing polyacrylamide gel. The 5'-boundary (FIG. 5B) was determined in an identical manner except that RNA radiolabeled at the 3'-end was used. Shown are RNase T$_1$ digest (lane 1), partial alkaline hydrolysis (lane 2), and hydrolytic fragments retained on nitrocellulose filters following incubation with VEGF at 5 nM (lane 3), 0.5 nM (lane 4), or 0.125 nM (lane 5). Arrows indicate the 3'- and the 5'-boundaries of the minimal ligand 12 (italicized).

Information Boundaries. In order to determine the minimal sequence information necessary for high-affinity binding to VEGF, deletion analyses were performed with representative members from each of the six families. These experiments were done by radiolabeling RNA ligands at either the 3' end or the 5' end (for the 3' or the 5' boundary determinations, respectively) followed by limited alkaline hydrolysis, partitioning of the free and the bound RNA by nitrocellulose filtration and resolving the hydrolytic fragments that retained high affinity for VEGF on denaturing polyacrylamide gels (Tuerk et al. (1990) J. Mol. Biol. 213:749). The combined information from the 3' and the 5' boundary experiments outlines the shortest sequence segment that has high affinity for the protein (FIG. 5) (SEQ ID NO:50). It is important to realize that these experiments define boundaries sequentially at the unlabeled ends of ligands in the context of full-length labeled ends. Since the full-length ends may provide additional contacts with the protein or participate in competing secondary structures, ligands truncated at both ends may have lower or higher affinities for the protein than their full-length parent. The following truncated ligands were prepared by in vitro transcription from synthetic DNA templates: l00t (Family 1) GGCCGGUAG-UCGCAUGGCCCAUCGCGCCGG (SEQ ID NO:51), 44t (Family 2) GGaaGCU-UGAUGGGUGACACACGUCAUGCCGAGCu (SEQ ID NO:52), 12t (Family 3) GGAAGGGAACCUGCGUCUCG-GCACCuucg (SEQ ID NO:53), 40t (Family 4) GGU-CAACGGUUGAGUCUGUCCCGuucgac (SEQ ID NO:54), 84t (Family 5) GgcucaaUAGUUGGAGGCCU-GUCCUCGCCGUAGAGC (SEQ ID NO:55) and 126t (Family 6) GGaACGGUUCUGUGUGUGGACUAGC-CGCGGCCGuu (SEQ ID NO:56) (letter t designates truncated sequences; underlined guanines are not present in the original sequences and were added to increase the transcriptional efficiency (Milligan et al. (1990) supra); lowercase letters indicate nucleotides from the constant sequence region). Binding curves for these truncated ligands and their dissociation constants are shown alongside their parent ligands in FIGS. 4A–F and Table 1. The dissociation constants of the truncated versus full-length ligands are generally comparable, although ligands 40t (SEQ ID NO:54) and 126t (SEQ ID NO:56) clearly bind to VEGF significantly less well than the corresponding full-length ligands.

Competition experiments revealed that binding of all possible pairwise combinations of truncated ligands representing each of the families is mutually exclusive (100t (SEQ ID NO:51), 44t (SEQ ID NO:52), 12t (SEQ ID NO:53), 40t (SEQ ID NO:54), 84t (SEQ ID NO:55) and 126t (SEQ ID NO:56)). Furthermore, all of these ligands are displaced by low-molecular weight (≅5,100 Da) heparin (data not shown). Truncated ligands and low-molecular weight heparin were used in these studies in order to maximize the probability of observing non-competing ligand pairs. It appears, therefore, that although there are multiple non-isomorphic solutions to high-affinity binding to VEGF, all examined ligands may bind to the same region of the protein. Proteins in general may have "immunodominant" domains for nucleic acid ligands.

EXAMPLE 3

Specificity of Truncated RNA Ligands to VEGF.

Binding of two truncated high-affinity ligands, 100t and 44t, to four other heparin binding proteins (bFGF, PDGF, antithrombin III and thrombin) was tested in order to address the question of specificity. Dissociation constants were determined using the nitrocellulose filter partitioning technique. Results are shown in Table 2. Binding of these ligands to VEGF in a buffer containing 10 mM dithiothreitol is at least 1000-fold weaker.

Figure 6:
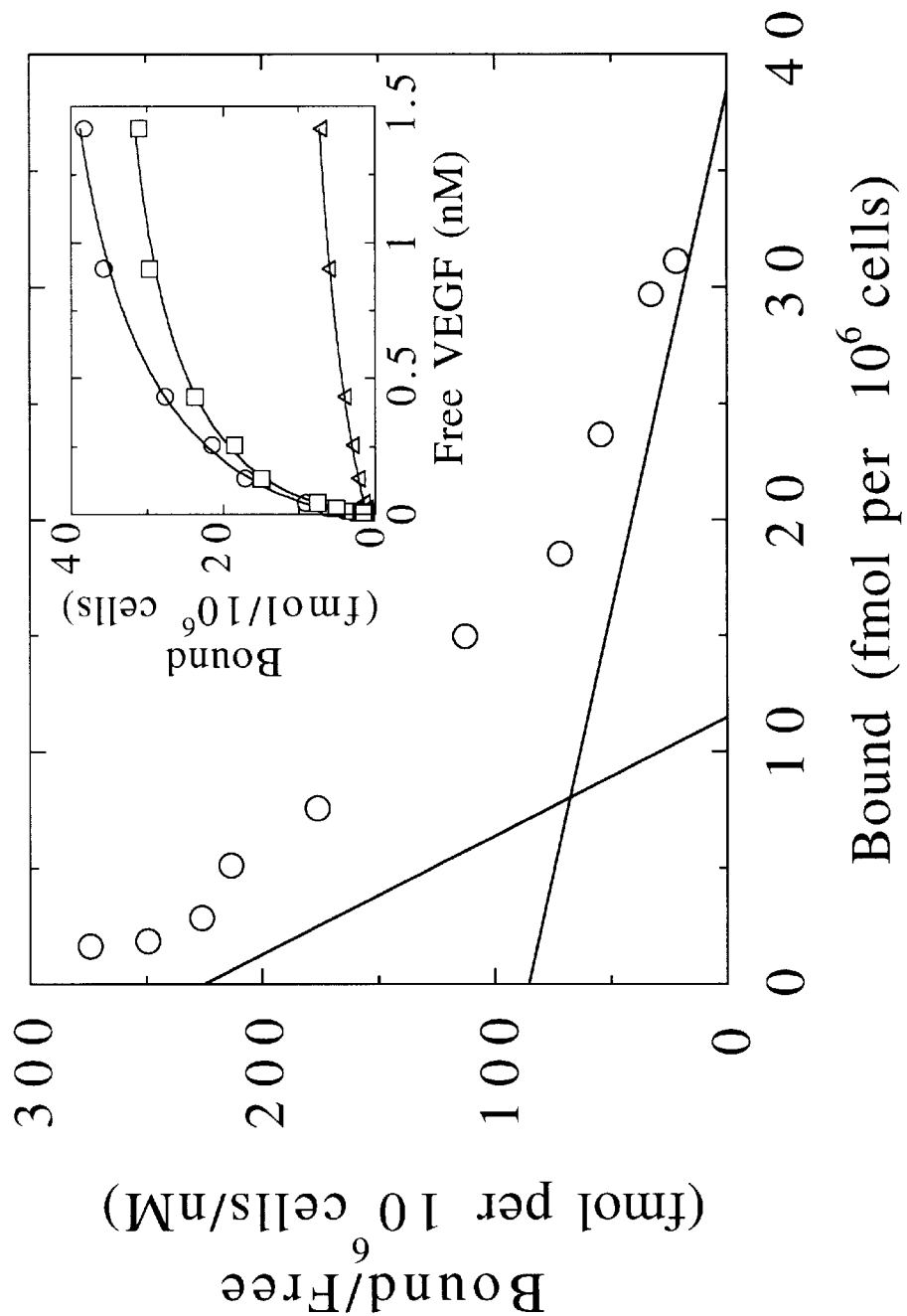
FIG. 6 shows the Scotchard analysis of $^{125}$I-VEGF binding to HUVECS. Data points are averages of two determinations. Increasing concentrations of $^{125}$I-VEGF were incubated with 2×10$^5$ cells in the presence or absence of 50-fold excess of unlabeled VEGF to determine the amount of total (o), specific (□) and non-specific (Δ) binding of $^{125}$I-VEGF as a function of free $^{125}$I-VEGF concentration (insert).

Receptor Binding. Unlabeled VEGF but not EGF was shown to inhibit binding of $^{125}$I-VEGF to HUVECs in a concentration-dependent manner (data not shown), confirming that $^{125}$I-VEGF binds to specific sites on HUVECs. As previous studies have reported (Myoken et al. (1991) Proc. Natl. Acad. Sci. USA 88:5819), two classes of receptors on HUVECs were observed to bind VEGF with dissociation constants of $\sim5\times10^{-11}$M (7,000 receptors/cell) and $\sim5\times10^{-10}$M (20,000 receptors/cell) (FIG. 6).

Figure 7:
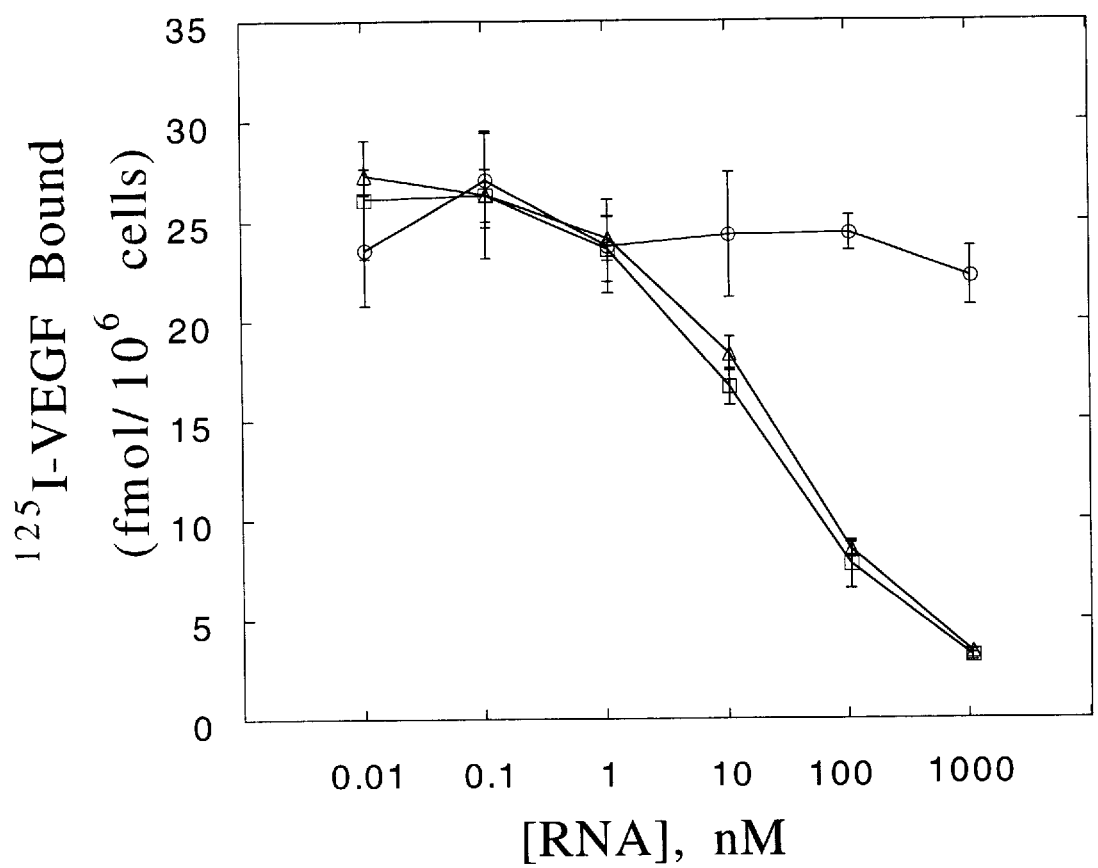
FIG. 7 shows the effect of random RNA (o) and representative high affinity RNA ligands 100t (SEQ ID NO:51) (family 1) (Δ) and 44t (SEQ ID NO:52)(family 2) (□) on binding of $^{125}$I-VEGF to cell-surface receptors as a function of RNA concentration. The inhibitory affect of high affinity ligands representing other sequence families is virtually identical to that of ligands loot and 44t.

A group of truncated RNA ligands representing each of the sequence families (100t, family 1; 44t, family 2; 12t, family 3; 40t, family 4; 84t, family 5; and 126t, family 6), as well as random RNA were tested for their ability to inhibit binding of VEGF to its cell-surface receptors. All high-affinity ligands, but not random RNA, inhibited VEGF-VEGF receptor interaction in a concentration-dependent manner with half-inhibition occurring in the 20–40 nM range (FIG. 7).

EXAMPLE 4

Modified 2'-NH$_2$ Pyrimidine RNA Ligands to VEGF.

In order to generate ligands with improved stability in vivo, two SELEX experiments (A and B) targeting VEGF were initiated with separate pools of randomized RNA containing amino (NH$_2$) functionalities at the 2'-position of each pyrimidine. Starting ligand pools for the two experiments contained approximately $10^{14}$ molecules (500 pmols) of modified RNA randomized at 30 (SELEX experiment A) and 50 (SELEX experiment B) contiguous positions. The starting RNAs and the corresponding PCR primers are defined in FIG. 8 (SEQ ID NOS:57–62). Sequences corresponding to the evolved regions of modified RNA are shown in FIGS. 9A–G.

Ligands with similar primary structures were grouped into 5 families and their consensus sequences are shown below each sequence set FIGS. 9A–G (SEQ ID NOS:63–146). Groups of sequences with similar primary structure (families) have been aligned in FIGS. 9A–G and their consensus sequences are shown below each set. Pairs of similar/related sequences, sequences that could not be included in any of the families ("other sequences") and sequences that correspond to ligands that bind additionally to nitrocellulose filters with high affinity have been shown in separate groups. Letter N in a sequence indicates an ambiguous position on a sequencing gel. Italicized letter N in a consensus sequence indicates a position that is not conserved (i.e., any nucleotide may be found at that position). Dissociation constants for Random RNA A (30N8), Random RNA B (50N7) and a set of modified (2'-amino pyrimidine high-affinity RNA ligands for VEGF are shown in Table 3.

TABLE 1

Dissociation Constants For a Representative Set of Full-Length and Truncated High-Affinity RNA Ligands for VEGF.[a]

| LIGAND[b] | Kd1 (nM)[c] | $\chi^{1d}$ | Kd2 (nM)[e] | SEQ ID NOS. |
|---|---|---|---|---|
| 100 | 0.20 ± 0.02 | 0.82 ± 0.02 | 42 ± 30 | 11 |
| 100t | 0.42 ± 0.04 | 0.76 ± 0.03 | 182 ± 94 | 51 |
| 44 | 1.7 ± 0.5 | 0.70 ± 0.11 | 38 ± 32 | 20 |
| 44t | 0.48 ± 0.04 | 0.73 ± 0.01 | 82 ± 23 | 52 |

TABLE 1-continued

Dissociation Constants For a Representative Set of Full-Length and Truncated High-Affinity RNA Ligands for VEGF.[a]

| LIGAND[b] | Kd1 (nM)[c] | $\chi^{1d}$ | Kd2 (nM)[e] | SEQ ID NOS. |
|---|---|---|---|---|
| 12 | 0.48 ± 0.07 | 0.56 ± 0.03 | 21 ± 5 | 22 |
| 12t | 1.1 ± 0.2 | 0.78 ± 0.04 | 180 ± 160 | 53 |
| 40 | 0.19 ± 0.09 | 0.19 ± 0.04 | 10 ± 1 | 28 |
| 40t[f] | 20 ± 1 | — | — | 54 |
| 84 | 0.82 ± 0.2 | 0.45 ± 0.06 | 21 ± 5 | 36 |
| 84t | 1.8 ± 0.4 | 0.53 ± 0.07 | 31 ± 10 | 55 |
| 126 | 0.14 ± 0.04 | 0.40 ± 0.04 | 11 ± 3 | 38 |
| 126t | 1.4 ± 0.2 | 0.54 ± 0.03 | 181 ± 57 | 56 |

[a]Binding experiments were done as described in Example 2 and errors are given as standard deviations.
[b]Full-length and truncated ligands are listed in pairs and represent sequence families 1–6, in order.
[c]Dissociation constant of the higher-affinity binding component as defined in eq. 5.
[d]Mole fraction of the high-affinity binding component as defined in eq. 5.
[e]Dissociation constant of the lower-affinity binding componenet as defined in eq. 5.
[f]Dissociation constant for ligand 40t was determined by fitting the data points to eq. 2.

TABLE 2

Binding of 100t and 44t Truncates

| Target Molecule | 100t (Kd) (SEQ ID. NO. 51) | 44t (Kd) (SEQ ID. NO. 52) |
|---|---|---|
| bFGF | 1 μM | 0.6 μM |
| PDGF | 0.6 μM | 0.6 μM |
| antithrombin III | 3 μM | 12 μM |
| thrombin | >10 μM | >10 μM |
| plasminogen activator inhibitor I | >10 μM | >10 μM |

TABLE 3

| Ligand | Kd1, nM | $\chi^1$ | Kd2, nM | SEQ ID NOS. |
|---|---|---|---|---|
| Rndm RNA A | 83 ± 21 | — | — | |
| Rndm RNA B | 240 ± 140 | — | — | |
| 14A | 0.70 ± 0.16 | 0.42 ± 0.05 | $\approx 10^2$ | 76 |
| 23A | 2.8 ± 0.3 | — | — | 78 |
| 24A | 0.71 ± 0.14 | 0.79 ± 0.5 | $\approx 10^2$ | 79 |
| 41A | 0.86 ± 0.19 | 0.68 ± 0.11 | $\approx 10^2$ | 93 |
| 17B | 0.028 ± 0.008 | 0.62 ± 0.05 | $\approx 10^2$ | 65 |
| 26B | 0.37 ± 0.10 | 0.74 ± 0.15 | $\approx 10^2$ | 82 |
| 30B | 0.034 ± 0.009 | 0.77 ± 0.06 | $10^1$–$10^2$ | 68 |
| 32B | 0.050 ± 0.023 | 0.50 ± 0.06 | 15 ± 9 | 104 |
| 34B | 0.068 ± 0.016 | 0.82 ± 0.06 | $10^1$–$10^2$ | 70 |
| 44B | 0.14 ± 0.06 | 0.54 ± 0.09 | 9 ± 6 | 95 |

We claim:

1. A method of identifying nucleic acid ligands to vascular endothelial growth factor (VEGF), comprising:
   a) contacting a candidate mixture of nucleic acids with VEGF, wherein nucleic acids having an increased affinity to VEGF relative to the candidate mixture may be partitioned from the remainder of the candidate mixture;
   b) partitioning the increased affinity nucleic acids from the remainder of the candidate mixture; and
   c) amplifying the increased affinity nucleic acids to yield a ligand enriched mixture of nucleic acids, whereby nucleic acid ligands to VEGF may be identified.

2. The method of claim 1 wherein said candidate mixture of nucleic acids is comprised of single stranded nucleic acids.

3. The method of claim 2 wherein said single stranded nucleic acids are ribonucleic acids.

4. The method of claim 1 further comprising:
   d) repeating steps a), b), c).

5. The method of claim 3 wherein said candidate mixture of nucleic acids comprises 2' position modified pyrimidines.

6. The method of claim 5 wherein said modified pyrimidines are 2 $NH_2$ modified pyrimidines.

* * * * *